United States Patent [19]

Lee et al.

[11] Patent Number: 5,348,886
[45] Date of Patent: Sep. 20, 1994

[54] METHOD OF PRODUCING RECOMBINANT EUKARYOTIC VIRUSES IN BACTERIA

[75] Inventors: Stephen C. Lee, St. Louis; Mark S. Leusch, Manchester; Verne A. Luckow, Chesterfield; Peter O. Olins, Glencoe, all of Mo.

[73] Assignee: Monsanto Company, St. Louis, Mo.

[21] Appl. No.: 941,363

[22] Filed: Sep. 4, 1992

[51] Int. Cl.$^5$ .................. C12N 15/00; C12N 15/86; C12N 15/11

[52] U.S. Cl. ................. 435/320.1; 435/69.1; 435/172.3; 435/252.3; 435/252.33; 536/23.1

[58] Field of Search ............ 435/69.1, 320.1, 172.3, 435/252.3, 252.33; 536/27, 23.1, 24.3

[56] References Cited

U.S. PATENT DOCUMENTS 4,745,051  5/1988  Smith et al. .................. 435/69.51
4,879,236  11/1989  Smith et al. .................. 435/235.1

OTHER PUBLICATIONS

Luckow, V. A. Protein Production and Processing From Baculovirus Expression Vectors. Insect Cell Cultures. To be published in 1993.

Barry, G. F. 1986 Permanent Insertion of Foreign Genes Into the Chromosome of soil Bacteria. Biotechnology vol. 4 May 1986 pp. 446–449.

Peakman, T. C., R. A. Harris, and D. R, Gewert. 1992. Highly efficient generation of recombinant baculoviruses by enzymatically medicated site-specific in vitro recombination. Nucleic Acids Res. 20:495–500.

Barry, G. F. A host range shuttle system for gene insertion into the chromosome of gram–negative bacteria. Gene 71(1988)75–84.

Patel, G., K. Nasmyth, and N. Jones. 1992. A new method for the isolation of recombinant baculovirus. Nucleic Acids Res. 20:97–104.

Luckow, V. A. 1991. Cloning and expression of heterologous genes in insect cells with baculovirus vectors., pp. 97–152. In A. Prokop, R. K. Bajpai, and C. Ho (ed.), Recombinant DNA Technology and Applications. McGraw-Hill, New York.

*Primary Examiner*—Richard A. Schwartz
*Assistant Examiner*—David Guzo
*Attorney, Agent, or Firm*—Dennis A. Bennett

[57] ABSTRACT

A method for producing infectious recombinant baculoviruses in bacteria is described. A novel baculovirus shuttle vector (bacmid) was constructed that contains a low-copy-number bacterial replicon, a selectable drug resistance marker, and a preferred attachment site for a site-specific bacterial transposon, inserted at a nonessential locus of the baculovirus genome. This shuttle vector can replicate in *E. coli* as a plasmid and is stably inherited and structurally stable after many generations of growth. Bacmid DNA isolated from *E. coli* is infectious when introduced into susceptible lepidopteran insect cells. DNA segments containing a viral promoter driving expression of a foreign gene in insect cells that are flanked by the left and right ends of the site-specific transposon can transpose to the attachment site in the bacmid propagated in *E. coli* when transposition functions are provided in trans by a helper plasmid. The foreign gene is expressed when the resulting composite bacmid is introduced into insect cells.

42 Claims, 5 Drawing Sheets

METHOD OF PRODUCING RECOMBINANT EUKARYOTIC VIRUSES IN BACTERIA

BACKGROUND OF THE INVENTION

FIELD OF THE INVENTION

This invention describes the production of eukaryotic virus shuttle vectors, and a novel method to produce recombinant virus shuttle vectors in bacteria.

Related Art

A wide variety of genes from viruses, fungi, plants, and animals have been expressed in insect cells infected with recombinant baculoviruses (Luckow, 1991; Luckow and Summers, 1988; Maeda, 1989; Miller, 1988; Murhammer, 1991; O'Reilly et al., 1992). Expression of the foreign gene is usually driven by the strong polyhedrin promoter of the Autographa californica nuclear polyhedrosis virus (AcNPV) which is transcribed during the late stages of infection. The recombinant proteins are often expressed at high levels in cultured insect cells or infected larvae and are, in most cases functionally similar to their authentic counterparts (Luckow, 1991; Luckow and Summers, 1988; Maeda, 1989; Miller, 1988; Murhammer, 1991; O'Reilly et al., 1992).

AcNPV has a large (130 kb) circular double-stranded DNA (dsDNA) genome with multiple recognition sites for many restriction endonucleases, and as a result, recombinant baculoviruses are traditionally constructed in a two-stage process. First, a foreign gene is cloned into a plasmid downstream from a baculovirus promoter and flanked by baculovirus DNA derived from a nonessential locus, usually the polyhedrin gene. This resultant plasmid DNA, is called a transfer vector and is introduced into insect cells along with wild-type genomic viral DNA. About 1% of the resulting progeny are recombinant, with the foreign gene inserted into the genome of the parent virus by homologous recombination in vivo. The recombinant virus is purified to homogeneity by sequential plaque assays, and recombinant viruses containing the foreign gene inserted into the polyhedrin locus can be identified by an altered plaque morphology characterized by the absence of occluded virus in the nucleus of infected cells.

The construction of recombinant baculoviruses by standard transfection and plaque assay methods can take as long as four to six weeks and many methods to speed up the identification and purification of recombinant viruses have been tried in recent years. These methods include plaque lifts (Summers and Smith, 1987), serial limiting dilutions of virus (Fung et al., 1988) and cell affinity techniques (Farmer et al., 1989). Each of these methods require confirmation of the recombination event by visual screening of plaque morphology (O'Reilly et al., 1992), DNA dot blot hybridization (Luckow and Summers, 1988), immunoblotting (Capone, 1989), or amplification of specific segments of the baculovirus genome by polymerase chain reaction techniques (Malitschek and Schartl, 1991; Webb et al., 1991). The identification of recombinant viruses can also be facilitated by using improved transfer vectors or through the use of improved parent viruses (O'Reilly et al., 1992). Co-expression vectors are transfer vectors that contain another gene, such as the lacZ gene, under the control of a second vital or insect promoter (Vialard et al., 1990; Zuidema et al., 1990). In this case, recombinant viruses form blue plaques when the agarose overlay in a plaque assay contains X-gal, a chromogenic substrate for β-galactosidase. Although blue plaques can be identified after 3–4 days, compared to 5–6 days for optimal vizualization of occlusion minus plaques, multiple plaque assays are still required to purify the virus. It is also possible to screen for colorless plaques in a background of blue plaques, if the parent virus contains the β-galactosidase gene at the same locus as the foreign gene in the transfer vector.

The fraction of recombinant progeny virus that result from homologous recombination between a transfer vector and a parent virus can be also be significantly improved from 0.1–1.0% to nearly 30% by using parent virus that is linearized at one or more unique sites near the target site for insertion of the foreign gene into the baculovirus genome (Kitts et al., 1990). Linear viral DNA by itself is 15- to 150-fold less infectious than the circular viral DNA. A higher proportion of recombinant viruses (80% or higher) can be achieved using linearized viral DNA (Hartig and Cardon, 1992; Kitts, 1992; Kitts, 1992; Kitts et al., 1990) (marketed as Bac-PAK6, Clonetech; or as BaculoGold, Pharmingen) that is missing an essential portion of the baculovirus genome downstream from the polyhedrin gene.

Peakman et al., (1992) described the use of the Crelox sytem of bacteriophage P1 to perform cre-mediated site-specific recombination in vitro between a transfer vector and a modified parent virus that both contain the lox recombination sites. Up to 50% of the viral progeny are recombinant. Two disadvantages of this method are that there can be multiple insertions of the transfer vector into the parent virus, and that multiple plaque assays are still required to purify a recombinant virus.

Recently Patel et al., (1992) described a rapid method for generating recombinant baculoviruses which is based on homologous recombination between a baculovirus genome propagated in the yeast Saccharomyces cervisiae and a baculovirus transfer vector that contains a segment of yeast DNA. The shuttle vector contains a yeast ARS sequence that permits autonomous replication in yeast, a CEN sequence that contains a mitotic centromere and ensures stable segregation of plasmid DNAs into daughter cells, and two selectable marker genes (URA3 and SUP4-o) downstream from the polyhedrin promoter ($P_{polh}$) in the order $P_{polh}$, SUP4-o, ARS, URA3, and CEN. The transfer vector contains the foreign gene flanked on the 5' end by baculovirus sequences and on the 3' end by the yeast ARS sequence. Recombinant shuttle vectors which lack the SUP4-o gene can be selected in an appropriate yeast strain in the presence of a toxic amino acid analogue. Insect cells transfected with DNA isolated from selected yeast colonies produce virus and express the foreign gene under control of the polyhedrin promoter. Since all of the viral DNA isolated from yeast contains the foreign gene inserted into the baculovirus genome and there is no background of contaminating parent virus, the time-consuming steps of plaque purification are eliminated. With this method, it is possible to obtain stocks of recombinant virus within 10–12 days. Two drawbacks, however, are the relatively low transformation efficiency of S. cervisiae, and the necessity for purification of the recombinant shuttle vector DNA by sucrose gradient prior to its introduction into insect cells.

The present invention overcomes many of the limitations discussed above by utilizing a novel baculovirus shuttle vector (bacmid) that replicates autonomously in bacteria and is infectious to susceptible lepidopteran insect cells (FIG. 1). The novel bacmid is a recombinant virus, constructed by standard techniques, that contains a bacterial replicon allowing it to be propagated and stably inherited in *Escherichia coli*. Bacmids containing target sites for site-specific transposons are recipients for transposons carried on other genetic elements. This approach not only greatly facilitates the use of baculovirus vectors for the expression of cloned foreign genes, but also permits the development of new strategies for rapid protein engineering of eukaryotic proteins and expression cloning of previously uncharacterized genes from cDNA libraries. Similar approaches could also be developed to aid in the construction of other large plasmid- and eukaryotic virus-based expression vectors.

SUMMARY OF THE INVENTION

In its broadest scope, the present invention provides a method to produce recombinant eukaryotic viruses in bacterial cells. The invention also relates to a composite shuttle vector, comprising:
  a. vital DNA which includes the elements required for said vital DNA propagation in eukaryotic host cells;
  b. A bacterial replicon, inserted into a nonessential locus of said viral DNA, which is capable of driving the replication of said viral DNA in bacteria;
  c. A first bacterial genetic marker inserted into a nonessential locus of said vital DNA;
  d. A preferential target site for the insertion of a transposon inserted into a nonessential locus of said viral DNA; and
  e. A transposon, inserted into said preferential target site, which includes heterologous DNA and a second bacterial genetic marker that is different than said first bacterial genetic marker.

The invention also covers novel donor vectors, novel bacmids, novel composite shuttle bacmids, and a novel method for making heterologous proteins by using the above, and a method for making the above.

BRIEF DESCRIPTION THE DRAWINGS

FIG. 1: Schematic outline for the generation of recombinant baculovirus shuttle vectors (bacmids) and site-specific transposon-mediated insertion of foreign genes into the baculovirus genome propagated in *E. coli* in which the donor plasmid and the helper are incompatible. Two other modes of this invention in which the donor DNA molecule is either a temperature-sensitive (ts) plasmid or the bacterial chromosome have been developed. We consider the method using the ts donor DNA molecule to be the best mode. All three modes are described in detail in the text.

FIG. 2: Flow chart for the construction of the bacmid transfer vectors pMON14271 and pMON14272. See text for details. The light gray sections represent baculovirus sequences flanking the polyhedrin promoter in the 7327 bp AcNPV EcoRI fragment I. The dark gray region represents the mini-F replicon derived as a BamHI/SalI fragment from the F' plasmid isolated from the *E. coli* strain DH5αF'IQ. The horizontal-striped section with a white center represents the lacZα region derived from pBCSKP containing an in-frame insertion of the attachment site for Tn7 (mini-attTn7). The left diagonally-striped section represents a segment conferring resistance to kanamycin.

FIG. 3: Flow chart for the construction of the mini-Tn7 donor plasmids. See text for details. The left and right ends of Tn7 and the polyhedrin promoter are indicated by solid areas. The heavy and light dotted areas represent the β-glucuronidase gene and the SV40 poly(A) termination signals, respectively. The left diagonally-striped section represents a segment conferring resistance to gentamicin. Wide hatched regions (SL2nx and SL2xb) represent synthetic polylinker regions derived from the superpolylinker plasmid pSL301. Open regions represent sections derived from the *E. coli* phoS and glmS genes flanking the target site attTn7 and sections containing the pUC origin of replication and the ampicillin resistance gene.

FIG. 4: The structure of baculovirus shuttle vectors (bacmids). The top map shows positions of EcoRI sites on a linear map of the AcNPV genome. The light gray section highlights EcoRI fragment I containing the polyhedrin gene and flanking regions. The maps of bMON17271 and bMON14272.H3 are linear representations of the mini-F-lacZα-mini-attTn7-Kan cassette inserted into the genome of AcNPV at the polyhedrin locus by homologous recombination. The maps of the bcMON14271::Tn14327 and bcMON14272::Tn14327 are linear representations of a portion of the composite bacmids derived by transpostion of the mini-Tn7 element from the donor plasmid pMON14327. A 3-fold enlargment of a linear representation of the entire donor plasmid pMON14327 is shown at the bottom of the figure. The arrow indicates the direction and expected size of a transcript containing the β-glucuronidase sequences initiated from the polyhedrin promoter. The shading of different genetic elements is the same as that described in the legends to FIG. 2 and FIG. 3. The maps are drawn to the scale (in bases) indicated by the bar at the right edge of each figure.

FIG. 5: SDS-PAGE of $^{35}$S-methionine-labeled proteins expressed by traditional recombinant baculoviruses and composite bacmid vectors. All viral stocks were titered and SF21 cells were infected at a multiplicity of infection of 10. Cells were radiolabeled at 44.5 hours post-infection for 4 hours with 10 $\mu$Ci $^{35}$S-methionine per $6 \times 10^5$ cells. The equivalent of $3.75 \times 10^4$ infected cells per lane were separated by electrophoresis on a 12% SDS-polyacrylamide gel. The gel was fixed, dried, and exposed to Kodak X-AR film ® for 76 hours at room temperature. The positions of Bio-Rad prestained molecular weight markers and expressed proteins are indicated.

| Lane | Virus | Description |
| --- | --- | --- |
| 1 | mock-infected cells | Uninfected cells |
| 2 | AcNPV | Wild-type virus expressing polyhedrin |
| 3 | vMON14271 | Parent bacmid containing mini-F-Kan-lacZα-mini-attTn7 |
| 4 | vMON14272 | Parent bacmid containing mini-F-Kan-lacZα-mini-attTn7 in opposite orientation |
| 5 | vcMON14271::14327 | Composite bacmid expressing β-glucuronidase |
| 6 | vchMON14271::14327/ pMON7124 | Composite bacmid expressing β-glucuronidase. DNA originally transfected into insect cells also contained pMON7124 helper plasmid |
| 7 | vcMON14272::14327 | Composite bacmid expressing β-glucuronidase |
| 8 | vMON14221 | Recombinant virus expressing β-glucuronidase constructed by |

-continued

| Lane | Virus | Description |
|---|---|---|
| | | classical method of homologous recombination in insect cells |
| 9 | vcMON14272::TnMON14314 | Composite bacmid expressing hLTA$_4$H |
| 10 | vchMON14271::TnMON22300/pMON7124 | Composite bacmid expressing a variant of hNMT. DNA originally transfected into insect cells also contained pMON7124 helper plasmid |

DEFINITIONS

As used throughout this specification, the following definitions apply for purposes of the present invention:

bacmid: A baculovirus shuttle vector capable of replication in bacteria and in susceptible insect cells.

bacteria: refers to any prokaryotic organism capable of supporting the function of the genetic elements described below. In the preferred mode, the bacteria should support the replication of the low copy number replicon operationally linked to the baculovirus in the bacmid, most preferably mini-F. The bacteria should support the replication of the donor plasmids, preferably moderate or high copy number plasmids or the host genome, most preferably either the bacteria chromosome, plasmids based on pMAK705, or plasmids based on pUC18. The bacteria should support the replication of helper plasmids, preferably moderate copy plasmids, most preferably based on pBR322. The bacteria should support the site-specific transposition of a transposon, most preferably one derived from Tn7. The bacteria should also support the expression and detection or selection of differentiable or selectable markers. In the preferred mode, the selectable markers are antibiotic resistance markers, most preferably genes conferring resistance to the following drugs: gentamicin, kanamycin, tetracycline, and ampicillin. In the preferred mode the differentiable markers should confer the ability of cells possessing them to metabolize chromogenic substrates. Most preferably, the differentiable marker encodes α-complementing fragment of β-galactosidase.

baculovirus: A member of the Baculoviridae family of viruses with covalently closed double-stranded DNA genome and which are pathogenic for invertebrates, primarily insects of the order Lepidoptera.

cis-acting: cis-acting elements are genes or DNA segments which exert their functions on another DNA segment only when the cis-acting elements are linked to that DNA segment.

composite bacmid: A bacmid containing a wild-type or altered transposon inserted into a nonessential locus, usually the preferential target site for the transposon.

donor plasmid: A plasmid containing a wild-type or altered transposon, preferably a mini-Tn7 transposon, composed of the left and right arms of Tn7 flanking a cassette containing a genetic marker, a promoter, and the gene of interest. The mini-transposon is on a pUC-based or pMAK705-based plasmid.

donor DNA molecule: Any replicating double-stranded DNA element such as the bacterial chromosome or a bacterial plasmid which carries a transposon capable of site-specific transposition into a bacmid. Preferably, the transposon contains a heterologous DNA and a genetic marker.

helper plasmid: A plasmid which contains a bacterial replicon, a genetic marker and any genes which encode trans-acting factors which are required for the transposition of a given transposon.

heterologous DNA: A sequence of DNA, from any source, which is introduced into an organism and which is not naturally contained within that organism.

heterologous protein: A protein which is synthesized in an organism, specifically from an introduced heterologous DNA, and which is not naturally synthesized within that organism.

locus: A specific site or region of a DNA molecule which may or may not be a gene.

mini-attTn7: The minimal DNA sequence required for recognition by Tn7 transposition factors and insertion of a Tn7 transposon or preferably mini-Tn7.

mini-F: A derivative of the 100 kb F plasmid which contains the RepF1A replicon, comprised of seven proteins including repE, and two DNA regions, oriS and incC, required for replication, maintenance, and regulation of mini-F replication.

mini-Tn7: A transposon derived from Tn7 which contains the minimal amount of cis-acting DNA sequence required for transposition, a heterologous DNA and a genetic marker.

nonessential: A locus is non-essential if it is not required for an organisms replication as judged by the survival of that organism following disruption or deletion of that locus.

$P_{polh}$: A very late baculovirus promoter which is capable of promoting high level mRNA synthesis from any gene, preferably a heterologous DNA, placed under its control.

plasmid incompatibility: Plasmids are incompatible if they interact in such a way that they cannot be stably maintained in the same cell in the absence of selection for both plasmids.

passage: Infection of a host with a virus (or a mixture of viruses) and subsequent recovery of that virus from the host (usually after one infection cycle).

preferential target site: A defined sequence of DNA specifically recognized and preferentially utilized by a transposon, preferably the attTn7 site for Tn7.

replicon: A replicating unit from which DNA synthesis initiates.

trans-acting: Trans-acting elements are genes or DNA segments which exert their functions on another DNA segment independent of the trans-acting elements genetic linkage to that DNA segment.

transposon: Any mobile DNA element, including those which recognize specific DNA target sequences, which can be made to move to a new site by recombination or in sertion and does not require extensive DNA sequence homology between itself and the target sequence for recombination. Preferably it is Tn7 which inserts preferentially into a specific target site (attTn7).

ABBREVIATIONS

The abbreviations used are: AcNPV, *Autographa californica* nuclear polyhedrosis virus; Amp, ampicillin; attTn7, attachment site for Tn7 (a preferential site for Tn7 insertion into bacterial chromosomes); bacmid, recombinant baculovirus shuttle vector isolated from *E. coli*; b, *E. coli*-derived bacmid; bc, *E. coli*-derived composite bacmid; bch, mixture of *E. coli*-derived composite bacmid and helper plasmid; Bluo-gal, halogenated indolyl-b-D-galactoside; bp, base pair(s); Cam, chloramphenicol; cDNA, complementary DNA; ds, double-stranded; Gen, gentamicin; IPTG, isopropyl-b-D-thiogalactopyranoside; Kan, kanamycin; kb, 1000 bp; PCR, polymerase chain reaction; r, resistant or resistance; s, sensitive; SDS-PAGE, sodium dodecyl sulfate polyacrylamide gel electrophoresis; Spc/Str, spectinomycin/streptomycin; Tet, tetracycline; Tn, transposon; tns, transposition genes; ts, temperature-sensitive; U, units; v, insect cell-derived baculovirus; vc, insect cell-derived composite baculovirus; vch, mixture of insect cell-derived composite baculovirus and helper plasmid; X-gal, 5-bromo-3-chloro-indolyl-$\beta$-D-galactopyranoside; X-gluc (5-bromo-3-chloro-indolyl-b-D-glucopyranoside), ::, transposon insertion.

ug, microgram,
ul, microliter
mg, milligram
ml, millititer

DETAILED DESCRIPTION OF THE INVENTION

Figure 1:
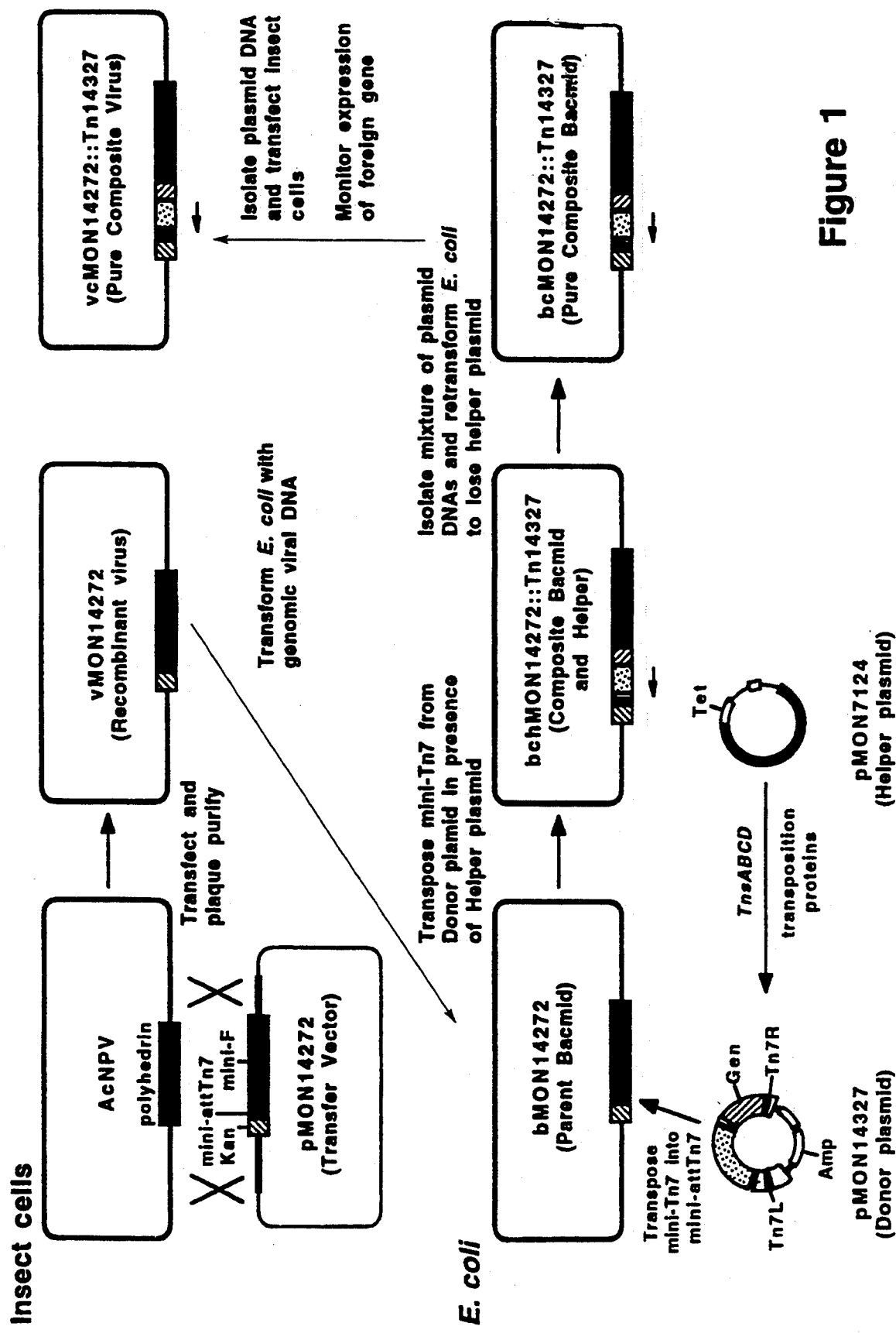

In this disclosure, we describe a novel strategy to efficiently generate recombinant baculoviruses by site-specific transposition in *E. coli*. Our new method eliminates many of the tedious steps of most current methods that rely on homologous recombination between a baculovirus transfer vector and genomic baculovirus DNA. We demonstrate that a baculovirus shuttle vector (bacmid) can be constructed that will replicate in *E. coli* as a large plasmid and remain infectious when introduced into insect cells. Using bacteria or preferably *E. coli* as a host to propagate the shuttle vector gives us a wide variety of genetic tools to manipulate and analyze the structure of the baculovirus genome. Recombinant virus (composite bacmid) DNA isolated from selected colonies is not mixed with parental, non-recombinant virus, eliminating the need for multiple rounds of plaque purification. As a result, this greatly reduces the time it takes to identify and purify a recombinant virus from 4–6 weeks (typical for conventional methods) to 7–10 days. One of the greatest advantages of this method is that it permits the rapid and simultaneous isolation of multiple recombinant viruses, and is particularly suited for the expression of protein variants for structure/function studies.

A baculovirus transfer vector was first constructed that contains a bacterial replicon, a selectable marker, and a preferential target site for a site-specific transposon. In the preferred mode, the baculovirus transfer vector contains a mini-F replicon (derived from the F' plasmid isolated from *E. coli* strain DH5αF'IQ) which allows for autonomous replication and stable segregation of plasmids at a low copy number (Holloway and Low, 1987; Kline, 1985), a selectable kanamycin resistance marker derived from Tn903 (Oka et al., 1981; Taylor and Rose, 1988; Vieira and Messing, 1982), and attTn7, the target site for the bacterial transposon Tn7 (Craig, 1989; Berg et al., 1989). Unlike most transposable elements, Tn7 inserts at a high frequency into the single attTn7 site located on the *E. coli* chromosome and into DNA segments carrying attTn7 on a plasmid. In the preferred mode, a mini-attTn7 is inserted into a DNA segment, also linked to the mini-F replicon and kanamycin resistance gene, which encodes the lacZα peptide. The insertion of the mini-attTn7 is such that it does not disturb the translational reading frame of the lacZα peptide. In the preferred mode, the mini-F-Kan-lacZα-mini-attTn7 sequences are inserted into a baculovirus transfer vector (derived from pVL1393) which lacks the baculovirus polyhedrin promoter and a portion of the polyhedrin coding sequences at the 5' end. Recombinant baculoviruses containing the mini-F-Kan-lacZα-mini-attTn7 cassette are generated by transfecting susceptible cultured insect cells with this transfer vector and wild-type genomic baculovirus DNA and are identified by their polyhedrin-minus phenotype in plaque assays and by DNA dot blot hybridization. In the preferred mode, the baculovirus that is used is the *Autographa californica* nuclear polyhedrosis virus (AcNPV) and the baculovirus transfer vector is derived from AcNPV. Susceptible host insect cells are derived from *Spodoptera frugiperda* (most preferably IPLB-SF21AE cells or its clonal isolate Sf9 cells), or from *Trichoplusia ni, Plutella xylostella, Manduca sexta,* or *Mamestra brassicae*. Calcium phosphate or lipofectin reagent is used to facilitate the transfection of the transfer vector and genomic viral DNA into susceptible insect cells. Recombinant vital DNA containing the mini-F-Kan-lacZα-mini-attTn7 cassette is isolated from infected insect cells and introduced into bacteria. In the preferred mode, the bacterial strain used is *E. coli* DH10B. The transformants, which replicate in bacteria under the control of the plasmid replicon are designated baculovirus shuttle vectors (bacmids). Bacmid DNAs transfected into susceptible host insect cell lines are infectious.

Donor replicons contain a transposon capable of site-specific transposition to its preferential target site present or in target bacmids. In the preferred mode, the site-specific transposon is derived from Tn7 and the preferential target site is the mini-attTn7 located on a baculovirus shuttle vector. The donor replicon is derived from pMON7117 which contains a deletion derivative of Tn7 (mini-Tn7) (Barry, 1988). The mini-Tn7 element on the donor plasmid is modified to contain a selectable drug resistance marker, a baculovirus promoter driving expression of a foreign gene, and a transcription termination poly(A) signal all flanked by the left and right ends of Tn7. In the preferred mode, the selectable marker confers resistance to gentamicin, the baculovirus promoter is the AcNPV polyhedrin promoter ($P_{polh}$), and the transcription termination poly(A) signal is derived from SV40. In the preferred mode, the transposable element resides on a donor replicon whose replication functions are provided by the chromosome, derived from a plasmid replicon which is incompatible with a helper plasmid, or most preferably derived from a temperature-sensitive plasmid replicon. The mini-Tn7 element on the donor replicon can transpose to the target plasmid (bacmid) when Tn7 transposition functions are provided in trans by a helper plasmid (FIG. 1). In the preferred mode, the helper plasmid is pMON7124, which contains the tnsABCDE genes of Tn7 inserted into a deletion derivative of pBR322. The helper plasmid pMON7124 confers resistance to tetracycline.

Using site-specific transposition to insert foreign genes into a baculovirus shuttle vector that is propagated in *E. coli* has a number of advantages over generation of recombinant baculoviruses in insect cells by homologous recombination. The mini-Tn7 donor plasmids we describe are small compared to traditional baculovirus trans,or vectors and are easily manipulated to add or remove restriction sites or different genetic elements. The efficiency of transposition of the mini- Tn7 element from the donor plasmid into the attachment site on the bacmid is high compared to generation of recombinants by homologous recombination. Insertions into the mini-attTn7 located in frame with a segment of DNA encoding the lacZα peptide on the bacmid prevent complementation between the α peptide produced by the bacmid and the acceptor polypeptide produced from a gone located on the chromosome of the bacteria. Therefore, transposon insertion events into the bacmid can be easily distinguished from insertions into the chromosome by screening for white colonies in a background of blue colonies on agar plates containing X-gal or Blue-gal. Bacmid DNA can easily be isolated from E. coli and its structure analyzed by restriction endonuclease digestion, Southern blotting or by DNA amplification using PCR techniques. Pure composite bacmid DNA, or a mixture of a composite bacmid DNA and a helper plasmid, can be transferred into insect cells to generate viruses which will express the foreign gone. Our results also indicate that it is not necessary to retransform the mixture of helper and composite bacmids into E. coli to select for the composite bacmid and eliminate the helper plasmid. Finally, the expression levels of foreign genes under the control of the polyhedrin promoter and inserted as a DNA segment into the baculovirus genome by transposition are similar to levels observed for recombinant viruses generated by homologous recombination in insect cells and purified by traditional methods.

It is recognized that a number of improvements to enhance or facilitate the use of the system as it is currently described can be envisioned, but which do not depart from the scope and spirit of the invention without compromising any of its advantages. These include substitution of different genetic elements (e.g., drug resistance markers, transposable elements, promoters, heterologous genes, and/or replicons, etc.) on the donor plasmid, the helper plasmid, or the shuttle vector, particularly for improving the efficiency of transposition in E. coli or for optimizing the expression of the heterologous gene in the host cell. The helper functions or the donor segment might also be moved to the attTn7 on the chromosome to improve the efficiency of transposition, by reducing the number of open attTn7 sites in a cell which compete as target sites for transposition in a cell harboring a bacmid containing an attTn7 site.

STARTING MATERIALS

Bacterial Strains

Brief descriptions of all the bacterial strains used in this work are shown in Table 1. *Escherichia coli* strain DH10B (Grant et al., 1990) was used as the host for all bacterial plasmid manipulations. *E. coli* strain DH5αF'IQ (Jessee and Blodgett, 1988) was used as the source of F' plasmid DNA. Both strains were obtained from GIBCO/BRL (Grand Island, N.Y.) as frozen competent cells.

TABLE 1

| | E. coli strains | |
|---|---|---|
| Designation | Genotype | Reference (Source) |
| DH5αF'IQ | F'proAB+ lacI$^q$ZΔM15 zzf::Tn5(Kan$^r$)/φ80dlacZΔM15 d(lacZYA-argF)U169 endA1 recA1 hsdR17 ($r_k^-$ $m_k^+$) deoR thi-1 supE44 λ$^-$ gyrA96 relA1 | (Jessee and Blodgett, 1988) (GIBCO/BRL) |
| DH10B | F$^-$ mcrA Δ(mrr-hsdRMS-mcrBC) φ80dlacZΔM15 ΔlacX74 endA1 recA1 deoR Δ(ara, leu)7697 araD139 galU galK nupG rpsL | (Grant et al., 1990) (GIBCO/BRL) |

Plasmids

Brief descriptions of all the plasmids used or constructed for this work are shown in Table 2.

TABLE 2

| | | Plasmids | | |
|---|---|---|---|---|
| Designation | Markers | Size | Description | Reference (Source) |
| F'lacIQ | Kan$^r$ | >90 kb | F'proAB+ lacI$^q$ZΔM15 zzf::Tn5(Kan$^r$) isolated from strain DH5αF'IQ | (Jessee and Blodgett, 1988) (GIBCO/BRL) |
| pBCSKP | Cam$^r$, lacZα | 3400 bp | pBC SK (+) phagemid cloning vector | (Stratagene) |
| pBS2SKP | Amp$^r$, lacZα | 2961 bp | pBlueScript II SK (+) phagemid cloning vector | (Alting-Mees and Short, 1989) (Stratagene) |
| pMAK705 | Cam$^r$, lacZα, ts replicon | ~5591 bp | pSC101$^{ts}$ replicon, Cam$^r$ from pBR325, polylinker and lacZα from pUC19 | (Hamilton et al., 1989) (Sidney Kushner) |
| pRAJ275 | Amp$^r$ | 4516 bp | pUC19-SalI/EcoRI + 1863 bp SalI/EcoRI GUS (β-glucuronidase) | (Jefferson et al., 1986) (Clonetech) |
| pSL301 | Amp$^r$, lacZα | 3284 bp | pBluescript KS(+)-derivative with SL2 super polylinker | (Brosius, 1989) (Invitrogen) |
| pUC-4K | Amp$^r$, Kan$^r$ | 3914 bp | pUC4-Kan (Tn903) | (Taylor and Rose, 1988; Vieira and Messing, 1982) (Pharmacia) |
| pMON3327 | Amp$^r$ | 2923 bp | pUC8-BamHI + 237 bp BamHI/BglII fragment of containing SV40 poly(A) signal | (Paul Hippenmeyer) |
| pMON7104 | Gen$^r$ | 5218 bp | pEMBL19P HincII + 1258 bp AluI fragment encoding the gene (aacC1) for gentamicin acetyltransferase-3-I (AAC(3)-I) | (Gerard Barry) |
| pMON7117 | Amp$^r$ | 11.2 kb | pUC8-attTn7::Tn7L-PiucA-lacZlacYlacA'-Tn7R | (Barry, 1988) (Gerard Barry) |
| pMON7124 | Tet$^r$ | 13.2 kb | pBR322-Tn7tnsABCDE genes-Tn7R | (Barry, 1988) (Gerard Barry) |
| pMON7134 | Amp$^r$ | 4483 bp | pEMBL9-attTn7 (523 bp HincII fragment into HincII site) | (Gerard Barry) |
| pMON14007 | Amp$^r$ | 11517 bp | pVL1393-BamHI + 1867 bp BamHI | (Gierse et al., |

TABLE 2-continued

| Designation | Markers | Size | Description | Reference (Source) |
|---|---|---|---|---|
| | | | fragement encoding hLTA$_4$H | 1992) |
| pMON14102 | Amp$^r$, Kan$^r$ | 4201 bp | pBS2SKP-PstI + 1240 bp PstI fragment of pUC-4K | This application |
| pMON14118 | Amp$^r$ | 9515 bp | pVL1393-EcoRI/SmaI to remove polyhedrin promoter | This application |
| pMON14181 | Kan$^r$ | 7965 bp | 6707 bp BamHI/EcoRI fragment of F'lacIQ + 1258 bp EcoRI/BamHI Kan$^r$ fragment of pMON14102 | This application |
| pMON14189 | Amp$^r$, Gen$^r$ | 4783 bp | pMON7117 PstI/XbaI + pMON7104 XbaI/PstI | This application |
| pMON14192 | Cam$^r$, lacZ$\alpha$ | 3463 bp | pBCSKP-SalI/EcoRI + 90 bp SalI/EcoRI PCR fragment of pMON7134 containing mini-attTn7 | This application |
| pMON14209 | Amp$^r$ | 5293 bp | pSL301 Stu I/Not I + pMON14007-EcoRV/Not I | This application |
| pMON14214 | Amp$^r$, Gen$^r$ | 4984 bp | pMON14189-BamHI/XbaI + 244 bp BamHI/XbaI SV40 poly-(A) fragment of pMON3327 | This application |
| pMON14221 | Amp$^r$ | 11510 bp | pMON14007-NcoI/EcoRI + NcoI/EcoRI fragment of pRAJ275 | This application |
| pMON14231 | Kan$^r$ | 8538 bp | pMON14181 NcoI/EcoRI/SalI + BbsI-cleaved lacZ$\alpha$-mini-attTn7 PCR fragment of pMON14192 | This application |
| pMON14239 | Amp$^r$, Gen$^r$ | 4526 bp | pMON14214-NcoI/NotI/Mung-bean nuclease | This application |
| pMON14255 | Amp$^r$, Gen$^r$ | 4554 bp | pMON14239-BamHI + I-SceI polylinker | This application |
| pMON14271 | Amp$^r$, Kan$^r$, lacZ$\alpha$ | 18053 bp | pMON14118-BglII + pMON14231-BamHI partial (A orientation) | This application |
| pMON14272 | Amp$^r$, Kan$^r$, lacZ$\alpha$ | 18053 bp | pMON14118-BglII + pMON14231-BamHI partial (B orientation) | This application |
| pMON14314 | Amp$^r$, Gen$^r$ | 6719 bp | pMON14255 XbaI + pMON14209 SpeI/NheI | This application |
| pMON14327 | Amp$^r$, Gen$^r$ | 6715 bp | pMON14314 NcoI/EcoRI+ pRAJ275 NcoI/EcoRI | This application |
| pMON18127 | Gen$^r$, lacZ$\alpha$, ts replicon | ~7771 bp | pMAK705 NdeI/Klenow/NruI + pMON14327 EcoO109/AlwNI partial | This application |

Plasmids pBS2SKP (Alting-Mees and Short, 1989) and pBCSKP were obtained from Stratagene (La Jolla, Calif.). Plasmid pMAK705 (Hamilton et al., 1989) was obtained from Dr. Sidney Kushner (University of Georgia, Athens, Ga.). Plasmids pRAJ275 (Jefferson et al., 1986) was obtained from Clonetech (Palo Alto, Calif.). pSL301 (Brosius, 1989) was obtained from Invitrogen (San Diego, Calif.). pUC-4K (Taylor and Rose, 1988; Vieira and Messing, 1982) was obtained from Phamacia LKB Biotechnology (Piscataway, N.J.). Plasmid pMON3327 was obtained from Dr. Paul Hippenmeyer (Monsanto Corporate Research, Chesterfield, Mo.). Plasmids pMON7104, pMON7117, pMON7124, and pMON7134 were obtained from Dr. Gerard Barry (Monsanto Agricultural Company, Chesterfield, Mo.). Plasmid pMON14007 (Gierse et al., 1992) was obtained from Dr. Verne Luckow (Monsanto Corporate Research, Chesterfield, Mo.). All other plasmids were constructed specifically for this work.

Bacterial Media

2XYT broth and LB broth and agar were prepared as described by (Miller, 1972). Supplements were incorporated into liquid and solid media at the following concentrations ($\mu$g/ml): Amp, 100; Gen, 7; Tet, 10; Kan, 50; X-gal or Bluo-gal, 100; IPTG, 40. Ampicillin, kanamycin, tetracycline, and IPTG (isopropyl-b-D-thiogalactoside) were purchased from Sigma Chemical Co. (St. Louis, Mo.). Gentamicin, X-gal (5-bromo-3-chloro-indolyl-$\beta$-D-galactoside), and Bluo-gal (halogenated indolyl-$\beta$-D-galactoside) were purchased from GIBCO/BRL.

Bacterial Transformation

Plasmids were transformed into frozen competent E. coli DH10B (Grant et al., 1990), obtained from GIBCO/BRL, using the procedures recommended by the manufacturer. Briefly, the frozen cells were thawed on ice and 33–100 $\mu$l of cells were incubated with 0.01–1.0 $\mu$g of plasmid DNA for 30–60 minutes. The cells were shocked by heating at 42° C. for 45 seconds, diluted to 1.0 ml with antibiotic-free S.O.C. buffer (GIBCO/BRL), and grown at 37° C. for 3 hours. A 0.1 ml sample of culture was spread on agar plates supplemented with the appropriate antibiotics. Colonies were purified by restreaking on the same selection plates prior to analysis of drug resistance phenotype and isolation of plasmid DNAs. Plasmids were also transformed into competent E. coli DH10B cells prepared by suspending early log phase cells in transformation and storage (TSS) buffer (Chung et al., 1989). TSS buffer, containing polyethylene glycol and dimethyl sulfoxide, was purchased from Epicentre Technologies (Madison, Wis.). In several experiments, plasmids were transformed into competent cells prepared by the calcium chloride method described by Sambrook et al., (1989).

DNA Preparation and Plasmid Manipulation

Large amounts of DNA were prepared from 250 ml cultures grown in 2XYT medium supplemented with appropriate antibiotics. Cultures were harvested and lysed by an alkaline lysis method and the plasmid DNA was purified over QIAGEN tip-500 resin columns (Studio City, Calif.) as described by the manufacturer. Small amounts of DNA from high copy number plasmids were prepared from 2 ml cultures using the rapid boiling method of Holmes and Quigley (1981) or using an alkaline lysis method and purification over Magic Mini Prep resin (Promega) as described by the manufacturer. All other standard genetic and cloning procedures were performed as described (Maniatis et al., 1982; Sambrook et al., 1989). Simulated cloning and manipulation of plasmid maps was facilitated through the use of POLLUX plasmid database and display program (Dayringer and Sammons, 1991).

Restriction enzymes BamHI, BglII, EcoRI, EcoRV, NcoI, NotI, PstI, ScaI, SmaI, XbaI, XhoI were purchased from Promega (Madison, Wis.) and used as recommended by the manufacturer. AluI, AlwNI, BbsI, DrdI, EcoO109, NheI, NruI, NdeI, PacI, and SpeI were purchased from New England Biolabs (Beverly, Mass.). I-SceI was purchased from Boehringer Mannheim (Indianapolis, Ind.). Large (Klenow) fragment of $E.\ coli$ DNA polymerase, T4 DNA ligase, and Mungbean nuclease were purchased from Promega (Madison, Wis.). Oligonucleotides were synthesized by Debbie Connors (Monsanto Corporate Research) or purchased from Midland Certified Reagents (Midland, Tex.).

Low-melting point agarose (GIBCO/BRL) was used to facilitate recovery of individual restriction fragments, when necessary. DNAs were separated on a 1% low-melting point agarose gel, stained with 2 μg/ml ethidium bromide for 15 minutes, and the products identified by illumination with a hand-held UV lamp. The desired band was cut out, 1/10 TE buffer added to a final volume of 500 μl, and melted at 65° C. Three μl of carrier tRNA (10 mg/ml in H$_2$O) was added to each tube followed by 500 μl of warm (65° C.) buffer-saturated phenol. The tubes were vortexed, spun at 14,000 rpm in a microcentrifuge for 5 min, and the aqueous phase transferred to a new tube. This was extracted with an equal volume of warm phenol/chloroform/isoamylalcohol (25:24:1), and the DNA in the aqueous phase concentrated by ethanol precipitation using ½ volume of 7.5M ammonium acetate or 1/10 volume 3M sodium acetate and two volumes cold (−20° C.) absolute ethanol and spinning for 15 min at 14,000 rpm. The DNAs were typically dissolved in 20 μl of 1/10 TE and a small sample analyzed by electrophoresis on a 1% agarose gel, to confirm the size and amount of the purified fragment. Where specified, DNA fragments were purified from agarose gels after absorbtion of the DNA to glass beads (QIAEX kit, QIAGEN, Studio City, Calif. or Gene Clean II Kit, Bio 101, LaJolla, Calif.) or by elution after electrophoresis of the DNA onto DEAE paper (Schleicher and Schuell, Keene, N.H.).

Insect Cell Culture and Propagation of Baculoviruses

Sf9 cells (Summers and Smith, 1987), a clonal isolate of the IPLB-SF21-AE cell line (Vaughn et al., 1977) derived from the ovarian tissue of the fall armyworm, *Spodoptera frugiperda*, were used for the propagation of wild-type and recombinant baculoviruses. The E2 strain (Smith and Summers, 1978; Smith and Summers, 1979) of the *Autographa californica* nuclear polyhedrosis virus (AcNPV) was used throughout these procedures. IPL-41 medium (GIBCO/BRL) supplemented with 2.6 g/l tryptose phosphate broth (GIBCO/BRL) and 10% fetal bovine serum (J.RH. Biosciences) was used for the routine propagation of Sf9 cells. Sf9 cells adapted for growth in Sf900 or Sf900-II serum-free medium (GIBCO/BRL) were also used for some experiments. Cells were maintained as monolayers in tissue culture flasks (Corning) or in suspension in spinner flasks (Bellco) at 100 rpm in a humidified incubator at 27° C. Transfections and plaque assays were performed as described by Summers and Smith (1987). Antibotics (Antibiotic-Antimycotic solution, GIBCO/BRL) were not usually added to the media used for the routine propagation of cultured cells, but were added to the agarose overlay in plaque assays. DNA dot blot hybridizations and all other routine cell culture methods are described by O'Reilly et al., (1992). Radiolabeling of infected cells with $^{35}$S-methionine was performed as described by Luckow and Summers (1988).

Construction of Traditional Baculovirus Transfer Vectors

Plasmid pMON14007 (Gierse et al., 1992) is a derivative of the baculovirus transfer vector pVL1393 containing the cDNA for human LTA$_4$ hydrolase under polyhedrin promoter control. Plasmid pMON14221 was constructed by replacing an NcoI/EcoRI fragment of pMON14007 containing the LTA$_4$H gene with an NcoI/EcoRI fragment of pRAJ275 containing the β-glucuronidase (GUS) gene. pRAJ275 is a derivative of pRAJ255 (Jefferson et al., 1986) containing a consensus $E.\ coli$ translational initiator in place of deleted 5' GUS sequences. Recombinant viruses constructed using pMON14007 and pMON14221 transfer vectors are used as controls for comparing levels of expression of LTA$_4$H and β-glucuronidase with composite bacmids. Recombinant viruses expressing β-glucuronidase were easily identified as blue plaques on agarose plates containing the chromogenic indicator, X-gluc (Luckow and Summers, A.T.C.C. Deposits The following have been deposited with the American Type Culture Collection at 12301 Parklawn Drive, Rockville, Md. 20852 U.S.A. $E.\ coli$ strains were deposited harboring the following replicons on Aug. 26, 1992.

bMON 14271.G2 A.T.C.C.#69059
bMON14272.H3 A.T.C.C.#69060
pMON 14327 A.T.C.C.#69061
pMON18127 A.T.C.C.#69062
pMON7124 A.T.C.C.#69063

In order to further illustrate the invention, the following exemplary laboratory preparative work was carried out.

EXAMPLE I

Construction of an Infectious Baculovirus Shuttle Vector

Figure 2:
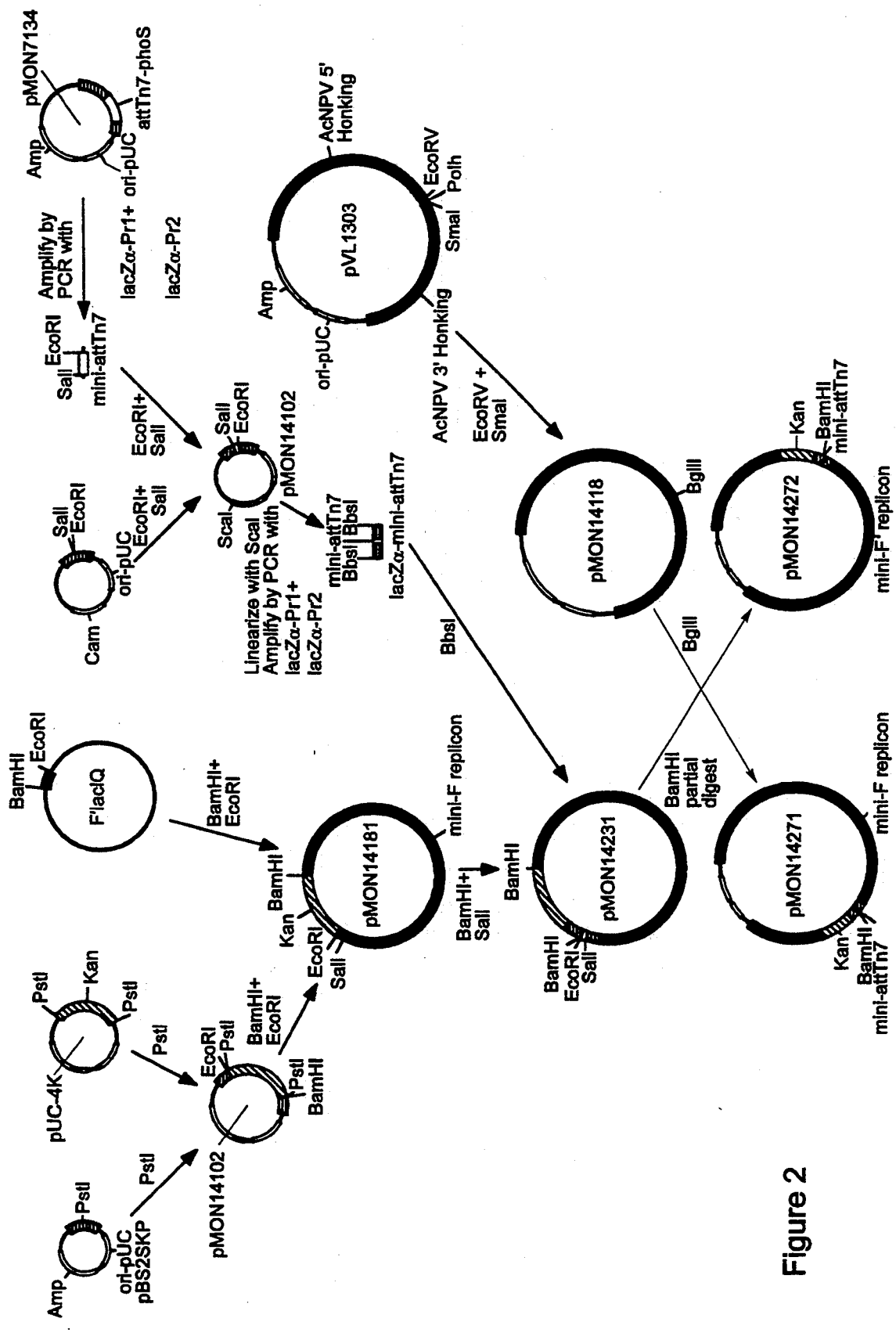

A flow chart describing construction of mini-Tn7 target plasmids is shown in (FIG. 2). Plasmid pMON14102 was constructed by cloning a 1240 bp PstI fragment of pUC4-K (Taylor and Rose, 1988; Vieira and Messing, 1982) into the PstI site of pBluescript II SK(+) (Airing-Mess and Short, 1989). F' plasmid DNA prepared from strain DH5a/(F'lac-pro)::Tn5 was digested with BamHI and EcoRI and ligated to an agarose gel-purified BamHI/EcoRI fragment from pMON14102 that confers resistance to kanamycin (Tn903). After transformation into $E.\ coli$ DH10B, kanamycin resistant colonies were selected and were shown to contain plasmids of the desired structure. The plasmid of one such transformant was designated pMON14181.

Plasmid pMON7134 was constructed by inserting a 523 bp HincII fragment of pEAL1 (Lichtenstein and Brenner, 1982) containing the attachment site for Tn7 (attTn7) into the HincII site of pEMBL9 (Dents et al., 1983). A 112 bp mini-attTn7 sequence was amplified by polymerase chain reaction (PCR) from the plasmid pMON7134 using two primers AttRP-PR1   (5'-   agatctgcag<u>gaatt</u>cacataacag-gaagaaaaatgc -3')[SEQ ID NO. 1] and AttSP-PR1 (5'- ggatcc<u>gtcga</u>cagccgcgtaacctggcaaa -3') [SEQ ID NO.2], designed to amplify a short DNA sequence containing a functional attTn7 with EcoRI (G'AATT,C) and SalI (G'TCGA,C) sites (double underlined above) at either end. PCR reactions were carried out using a DNA Thermal Cycler and GeneAmp PCR reagent kit (Perkin Elmer Cetus, Norwalk, Conn.). Thirty cycles were used to amplify the mini-attTn7. Each cycle consisted of three steps, denaturation of double stranded DNA (94° C., 1 min), annealing of oligonucleotide primers (50° C., 2 min), and polymerization of the complementary DNA strand (72° C., 3 min). The amplified segment contains an 87 bp attTn7 (numbered −23 to +61 as described by Craig (1989). The 112 bp amplified fragment was digested with EcoRI and SalI and cloned into the EcoRI and SalI sites within the lacZα region of the cloning vector pBCSKP to generate pMON14192. The EcoRI/SalI mini-attTn7 does not disrupt the reading frame of the lacZα region of pBCSKP and has the E. coli glmS transcriptional terminator inserted in the opposite orientation from transcription directed by the Lac promoter, so colonies of E. coli strain DH10B harboring pMON14192 are blue on agar plates containing X-gal or Bluo-gal.

Plasmid pMON14192 was linearized with ScaI and used as a template for PCR in the presence of two new primers, lacZA-PR1    (5'-tgatcatt<u>aatt</u>aagtcttcgaaccaatacg-caaaccgcctctccccgcgcg-3') [SEQ ID NO.3] and IacZA-PR2 (5'- cgatcgact<u>cgag</u>cgtcttcgaagcgcgtaac-caccacaccegccgcgc -3'), [SEQ ID NO.4]

as described above, except the reaction buffer contained 5% (v/v) DMSO to permit less stringent annealing. Thirty cycles were used to amplify the mini-attTn7. Each cycle consisted of three steps, denaturation of double stranded DNA (94° C., 1 min), annealing of oligonucleotide primers (55° C., 2 min), and polymerization of the complementary DNA strand (72° C., 3 min). The PCR primers were designed to amplify the entire lacZα region of pMON14192 or any pUC-based cloning vectors. Each primer contained a BbsI site (GAAGACNN'NNNN,[SEQ ID NO.5] or ,NNNN'NNGTCTTC [SEQ ID NO6]) near their 5' ends. Primer lacZA-PR1 contains an EcoRI-compatible ('AATT,) site and primer IacZA-PR2 contains a SalI-compatible ('TCGA,) site as part of the cleavage site (double underline above) flanking the BbsI recognition site (single underline above). A DrdI site and a PacI site (not underlined) are also adjacent to the BbsI sites in lacZA-PR1 and lacZA-PR2, respectively. The amplified 728 bp dsDNA fragment could therefore be cleaved with BbsI to generate EcoRI-and SalI-compatible sticky ends, even though there were internal EcoRI and SalI sites flanking the mini-attTn7 region towards the center of the fragment. The 708 bp BbsI-cleaved PCR fragment was ligated to pMON14181 (mini-F-Kan) that was cleaved with EcoRI and SalI and transformed into E. coli DH10B. Several kanamycin-resistant Lac+ transformants were obtained, and all had the expected DNA structure. One clone, designated pMON14231 (mini-F-Kan-lacZα-mini-attTn7) was chosen for subsequent work. Its structure was verified by digestion with BamHI, EcoRI, EcoRV, KpnI, BglII, HindIII, and HindIII plus BglII (data not shown).

Plasmid pMON14118 was constructed by digesting pVL1393 (Luckow, 1991; O'Reilly et al., 1992) with EcoRV and SmaI and recircularizing in the presence of T4 DNA ligase to remove the AcNPV polyhedrin promoter. Plasmid pMON14231 has two BamHI sites, one within the lacZα-mini-attTn7 region and the other at the junction between the mini-F and Kan genetic elements, so it was digested with a low concentration of is BamHI to generate full-length linear molecules and ligated to the pMON14118 cleaved with BglII to generate pMON14271 and pMON14272. Plasmids pMON14271 and pMON14272 differ only in the orientation of the mini-F-Kan-lacZα-mini-attTn7cassette inserted into the pMON14118 transfer vector. Their structures were verified by digestion with BamHI, EcoRI, and XhoI. Upon transformation into E. coli DH10B, both plasmids confer resistance to ampicillin and kanamycin and have a Lac+ phenotype on plates containing X-gal or Bluo-gal.

Both transfer vectors, pMON14271 and pMON14272, were introduced into insect cells along with wild-type genomic AcNPV DNA using a calcium phospate-mediated transfection protocol (Summers and Smith, 1987). Putative recombinant viruses were identified by their occlusion minus phenotype under a stereo dissecting microscope and confirmed by DNA dot blot hybridization using $^{32}$P-labeled pMON14181 DNA prepared by random priming (O'Reilly et al., 1992) as a probe to cell lysates (Summers and Smith, 1987) blotted 48 hr post infection onto nitrocellulose filter paper (Luckow and Summers, 1988). Three viruses for each construct were selected and purified free from wild-type parental virus by sequential plaque assays (Summers and Smith, 1987) and passage 1 stocks of each purified virus (vMON14271 and vMON14272) were prepared. The prefix v is used to designate the source of viral stocks or vital DNA, in this case prepared from infected insect cells.

Genomic viral DNA was prepared from the infected cells used to generate the passage 1 stock of virus using the protocol described by Summers and Smith (Summers and Smith, 1987). Vital DNA constitutes approximately 25% of the total nucleic acid content of an infected cell nucleus very late in infection (>48 hr p.i.). Briefly, cells were lysed with lysis buffer (30 mM Tris-HCl, pH 8.0, 10 mM Mg acetate, and 1% Nonidet P-40), and the nuclei pelleted by centrifugation at 2000 rpm for 3 minutes. The nuclei were washed once in cold PBS and lysed with 4.5 ml extraction buffer (100 mM Tris-HCl, pH 8.0, 100 mM EDTA, 200 mM KCl). Approximately 200 μg of proteinase K was added and incubated at 50° C. for 1 hour before adding 0.5 ml 10% Sarcosyl and incubating at 50° C. overnight. The DNA was purified by extracting once with buffer-saturated phenol and once with phenol/chloroform/isoamyl alcohol (25:24:1) before precipitating with ethanol.

Viral DNA was transformed into E. coli DH10B using frozen competent cells obtained from GIB-CO/BRL. Colonies on plates transformed with the viral DNAs vMON14271 or vMON14272 were kanamycin resistant and gave a Lac+ (blue) phenotype in the presence of Bluo-gal or X-gal indicating complementation between the lacZα peptide expressed by the plasmid and the lacZΔM15 acceptor polypeptide expressed from the chromosome of *E. coli* DH10B. The transformants were designated bMON14271.G2 and bMON14272.H3 to indicate their bacterial origin. Small amounts of pure bacmid DNA could be isolated from *E. coli* after alkaline lysis and purification over resin columns. These results indicated that the insect cell-derived baculovirus DNA could be propagated in *E. coli* using the mini-F replicon which ensures stable replication of plasmid DNAs at a low copy number. No transformants were observed when wild-type viral DNA or recombinant virus DNA lacking the mini-F region were introduced into *E. coli*.

Bacmid DNA isolated from *E. coli* was introduced into insect cells using the calcium-phosphate transfection protocol (Summers and Smith, 1987). Three to five days post transfection the cells appeared swollen and detached easily from the plastic bottom of the flask like cells infected with viral DNA isolated originally from insect cells. Mock-infected cells attached tightly to the monolayer. Plaques produced by budded virus generated from transfections using *E. coli*-derived bacmid DNA were all occlusion minus (data not shown).

EXAMPLE II

Construction of a Mini-Tn7 Donor Plasmid

To facilitate the construction and delivery by transposition of mini-Tn7 elements from a donor plasmid to the attTn7 sequence present in a target plasmid, the replicon containing the element should be of small size, moderate or high copy number, and contain a drug resistance marker and a polylinker with unique restriction sites between the left (Tn7L) and right (Tn7R) arms of Tn7.

Figure 3:
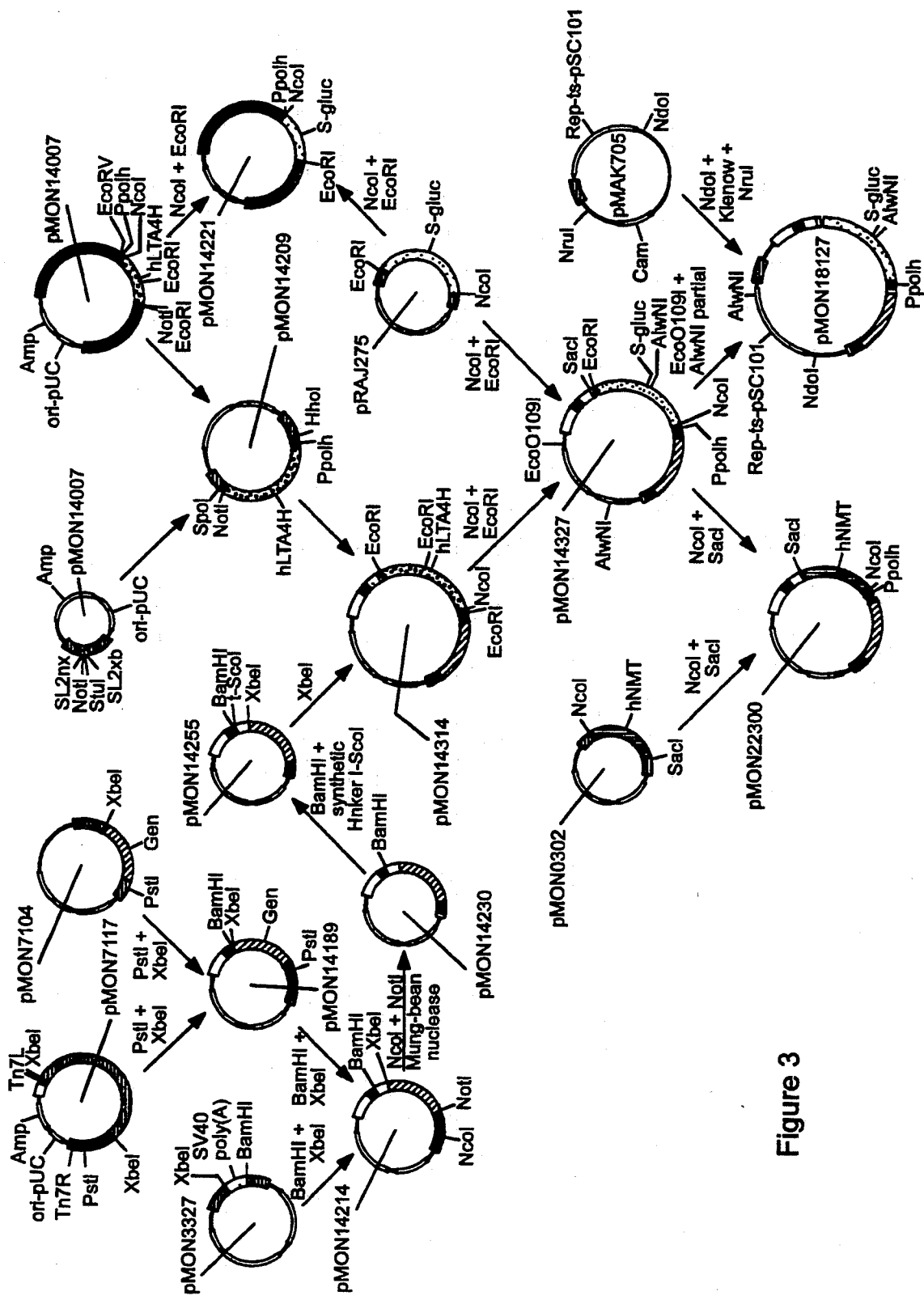
Figure 4:
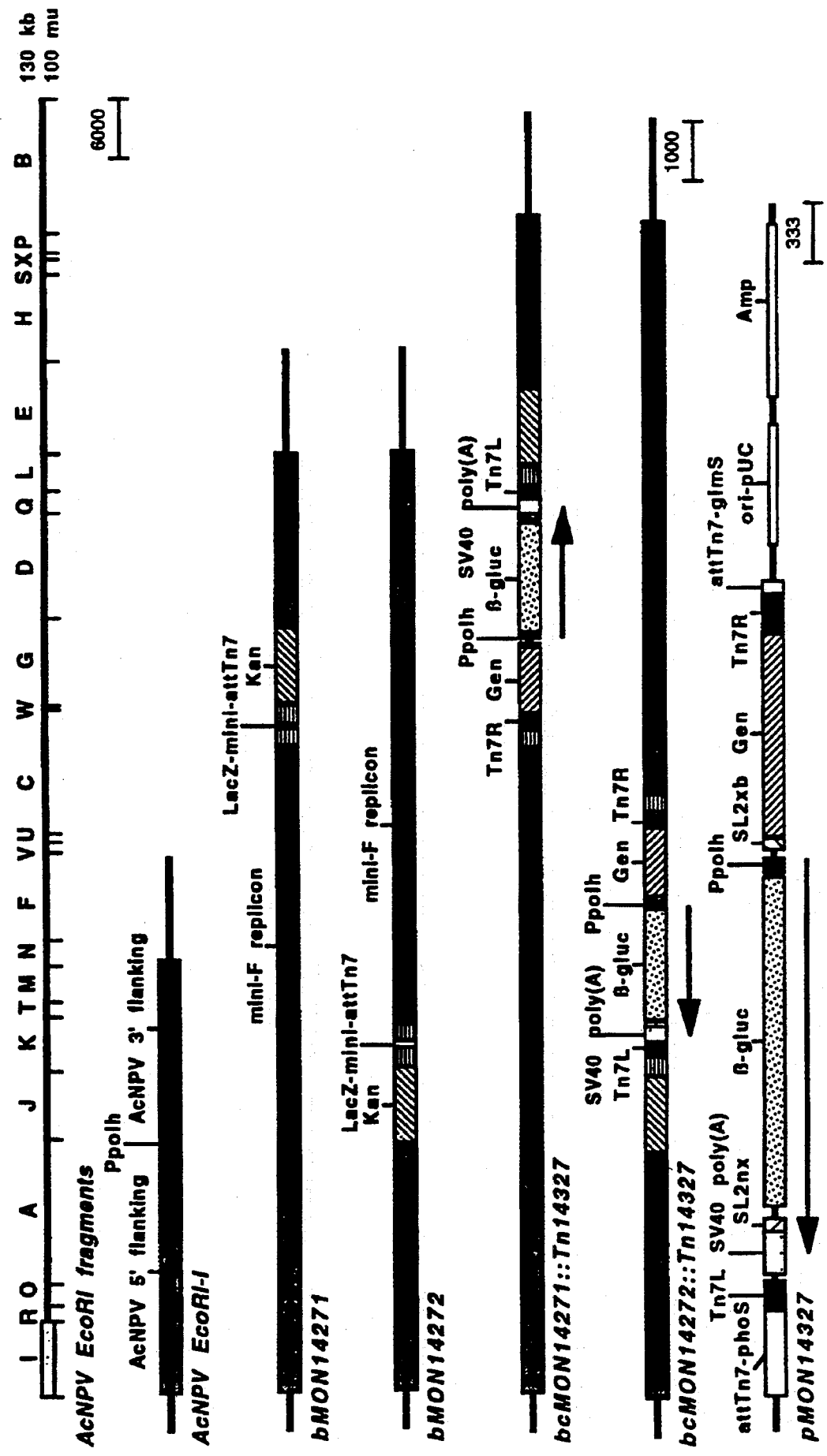

A flow chart describing construction of mini-Tn7 donor plasmids is shown in FIG. 3. Plasmid pMON7104 (G. Barry, unpublished) is a derivative of pEMBL19P containing a 1258 bp AluI fragment encoding the gene (aacC1) for gentamicin acetyltransferase-3-I (AAC(3)-I) (Wohlleben et al., 1989). The gentamicin resistance gene of pMON7104 was released by XbaI/PstI digestion and the resultant fragment was ligated to PstI/XbaI-digested pMON7117 (Barry, 1988), producing pMON14189. The SV40 poly-(A) transcription termination signal of pMON3327 (P. Hippenmeyer, unpublished) was released as a 244 bp fragment by BamHI/XbaI digestion and ligated to BamHI/XbaI-digested pMON14189, resulting in plasmid pMON14214. pMON14214 was digested with NcoI and NotI and the restriction fragment sticky ends were removed by treatment with Mung-bean nuclease (Promega) using conditions described by the manufacturer. This fragment was recircularized by ligation, producing pMON14239. pMON14239 was digested with BamHI and ligated to the synthetic double-stranded polylinker shown below (Boehringer Mannheim Biochemica), resulting in plasmid pMON14255. Omega nuclease I-SceI recognizes the 18 bp sequence TAGGG,ATAA'CAGGGTAAT[-SEQ ID NO.7] and generates a four bp 3' hydroxyl overhang (Colleaux et al., 1988).

| BamHI | I-SceI | BglII |
|---|---|---|

Linker I-SceI (5'-gatccgctaggg ataa cagggtaatata-3')[SEQ ID NO. 8]

(Megalinker) (3'-gcgatccc,tatt gtcccattatatctag-5')[SEQ ID NO. 9]

Plasmid pMON14007 (Gierse et al., 1992) was digested with EcoRV and NotI and the fragment containing the AcNPV polyhedrin promotor and the human leukotriene $A_4$ hydrolase cDNA ($hLTA_4H$) (Funk et al., 1987; Minami et al., 1987) was ligated to StuI/NotI-digested pSL301 (Brosius, 1989), producing plasmid pMON14209. pMON14209 was digested with SpeI and NheI and the fragment containing the polyhedrin promoter and $hLTA_4H$ gene was ligated to XbaI-digested pMON14255, resulting in plasmid pMON14314. Plasmid pMON14327 was constructed by replacing the $hLTA_4H$ gene of pMON14314 with an NcoI/EcoRI fragment of pRAJ275 (Jefferson et al., 1986) which contains the coding sequences for the β-glucuronidase gene. The plasmid pMON22300 is a derivative of the donor plasmid pMON14327 that has the cDNA for human myristoyl CoA:protein N-myristoyl transferase (Duronio et al., 1992) (hNMT) under the control of polyhedrin promoter. The hNMT cDNA in this plasmid has a Pro to Leu mutation at amino acid position 127. The resulting donor plasmids pMON14314, pMON14327, and pMON22300, therefore, have mini-Tn7 elements on a pUC-based plasmid containing a gentamicin resistance marker, the polyhedrin promoter driving expression of a foreign gene, a polylinker, an SV40 poly(A) transcriptional termination signal, and I-SceI site between the left and right arms of Tn7. These donor molecules are incompatible with the helper plasmid, pMON7124. This plasmid incompatibility can be used to eliminate the donor molecule after transposition to bacmid has occurred (See Example V). The gentamicin resistance marker is used to select for transposition events to the target plasmid and the I-SceI site is used to facilitate the mapping of mini-Tn7 elements inserted into the genome of the target bacmids.

EXAMPLE III

Construction of a Temperature-Sensitive Mini-Tn7 Donor Plasmid

The donor molecules based on plasmid incompatability (refer to Example II) were sufficient to validate the concept of site-specific transposition for this invention. An alternative and more efficient method is the use of a temperature-sensitive donor plasmid. The temperature-sensitive (ts) plasmid pMAK705 (Hamilton et al., 1989) containing a ts pSC101 origin of replication and β-galactosidase gene was digested sequentially with NruI and NdeI. The ends were filled and dephosphorylated as described (Sambrook et al., 1989) and the 2.5 kb fragment containing the ts replicon and the β-galactosidase gene were isolated from 0.7% agarose using NA45 DEAE membrane according to the manufacturer's protocol with the following exception; after elution from the NA45 membrane in 300 μl high salt NET buffer, the fragment was concentrated using a Geneclean II kit into 15 μl sterile water. pMON14327 was linearized with EcoO109 and the ends filled. The linearized/filled pMON14327 was partially digested with 0.1 U AlwNI and immediately purified from enzyme using a Geneclean II kit. The DNA was treated with 0.25 U Mung-bean nuclease as described in the manufacturers protocol. The 5.2 kb fragment containing Tn7R, a gentamicin resistance gene, the AcNPV polyhedrin promoter driving a β-glucuronidase gene, an SV40 poly-(A) signal, and Tn7L was isolated from 0.7% agarose using NA45 DEAE membrane as described above. This fragment was mixed and ligated with the 2.5 kb NdeI/NruI fragment from pMAK705. The resulting plasmid, pMON18127, was transformed into competent E. coli DH10B cells and outgrown at 30° C. Cells were plated on LB agar medium containing 10 μg/ml gentamicin, 40 μg/ml IPTG and 200 μg/ml Bluo-gal and incubated at 30° C. Blue colonies were picked and purified at 30° C. Verification of the ts phenotype was accomplished by diluting 12 independent isolates in 2 ml LB each and patching onto each of two plates of LB agar medium containing 10 μg/ml gentamicin, 40 μg/ml IPTG and 200 μg/ml Bluo-gal. One plate of each pair was incubated at 30° C. the other at 44° C. Clones which gave rise to colonies on plates incubated at 30° C. but not at 44° C. were selected as ts (Hashimoto and Sekiguchi, 1976; Hashimoto-Gotoh and Sekiguchi, 1977). The structure of temperature-sensitive pMON18127 was confirmed by restriction analysis.

EXAMPLE IV

Insertion of Mini-Tn7 Into the Chromosome

As an alternative to plasmid-based donor molecules, the mini-Tn7 element from pMON14327 was inserted into the chromosomal attTn7 site of E. coli DH10B. In this system the new strain of E. coli containing the mini-Tn7 element from pMON14327 will be designated DH10B::Tn14327.

One hundred μl MAX Efficiency E. coli competent cells DH10B were transformed with 30 ng of helper plasmid pMON7124. Transformants were selected on LB agar medium containing 15 μg/ml tetracycline. Competent cells were prepared using a modified $CaCl_2$ method described by (Sambrook et al., 1989). Briefly, a single purified colony was grown overnight in 2XYT medium containing 15 μg/ml tetracycline. Ten ml of pre-warmed 2XYT medium containing 15 μg/ml tetracycline was inoculated with 200 μl of the overnight culture and grown at 37° C. to a Klett=100. Two ml of cells were centrifuged at 5K for 10 minutes in a JA-17 rotor (Beckman) at 4° C. and the pellet resuspended gently in 1 ml ice-cold 0.1M $CaCl_2$ and incubated on ice for 15 minutes. The cells were centrifuged as above and the pellet gently resuspended in 200 μl ice-cold 0.1M $CaCl_2$. One hundred μl of the competent cells were transformed with 500 ng of donor plasmid pMON14327. Transformants were selected on LB agar medium containing 10 μg/ml gentamicin and 15 μg/ml tetracycline and purified by streaking onto LB agar medium containing 10 μg/ml gentamicin. Isolated colonies were scored for ampicillin sensitivity by patching to LB agar medium containing 100 μg/ml ampicillin as described above. A gentamicin-resistant, ampicillin-sensitive colony was inoculated into 10 ml LB medium without antibiotic and grown overnight at 37° C. The overnight culture was then serial diluted to $10^{-7}$ cells/ml and grown in LB overnight at 37° C. This entire outgrowth procedure was repeated a total of 4 times. Cells from the fourth overnight were diluted in LB medium to $10^{-4}$, $10^{-5}$ and $10^{-6}$ cells/ml. One hundred μl of each dilution was plated onto LB agar medium and grown overnight at 37° C. Colonies from the $10^{-5}$ and $10^{-6}$ cells/ml dilutions were replica plated onto LB agar medium containing 15 μg/ml tetracycline and grown overnight an 37° C. Colonies from the master plate which did not grow as replicates on the medium containing 15 μg/ml tetracycline were streaked onto LB agar containing 10 μg/ml gentamicin and Grown overnight at 37° C. isolated colonies were confirmed to be both ampicillin and tetracycline sensitive as described. Total cellular DNA was isolated by SDS lysis as described (Ausubel et al., 1989). Insertion of the mini-Tn7 element into the chromosomal attTn7 site was confirmed by PCR using primers specific for the chromosome and the mini-Tn7 element (data not shown). Wild-type DH10B chromosomal DNA was used as a control.

EXAMPLE V

Transposition of Mini-Tn7 Elements from a Donor Molecule to a Target Bacmid

Transposition experiments using incompatible donor plasmids.

Transposition experiments were carried out by transforming a donor plasmid (pMON14314, pMON14327, or pMON22300) conferring ampicillin- and gentamicin-resistance into competent E. coli DH10B cells harboring the tetracycline-resistant helper plasmid pMON7124 and a kanamycin-resistant, lacZα+ bacmid (bMON14271.G2 or bMON14272.H3) and plating the cells out on LB agar plates containing kanamycin, tetracycline, gentamicin, X-gal, and IPTG. White (Lac−) kanamycin-resistant, gentamicin-resistant, and tetracycline-resistant, but ampicillin-sensitive colonies harboring the helper plasmid and the bacmid with the mini-Tn7 element inserted into the mini-attTn7 region of the lacZα region, which arose at a frequency of between 5% and 25% of the total colonies, were identified and purified by restreaking on the same plates. Blue(Lac+), kanamycin-, gentamicin-, tetracycline-resistant, but ampicillin-sensitive colonies, which probably represent insertions of the mini-Tn7 element into the attTn7 site in the E. coli chromosome between the glmS and phoS genes, occurred at a nearly equivalent frequency. The remainder of the colonies were blue (Lac+), and conferred resistance to all four antibiotics. Although these simultaneously harbored the bacmid shuttle vector, the helper, and the donor plasmid, this situation appeared to be unstable as white (Lac−) and blue (Lac+) colonies that were also kanamycin-resistant, tetracycline-resistant, and gentamicin-resistant, but ampicillin-sensitive appeared upon restreaking. Plasmid DNAs were purified from white kanamycin-, gentamicin-, and tetracycline-resistant, but ampicillin-sensitive colonies harboring the helper plasmid and the composite bacmid with the mini-Tn7 element inserted into the mini-attTn7 region of the lacZα region over QIAGEN resin columns. This mixture of plasmid DNAs was used to retransform E. coli DH10B, selecting for kanamycin and gentamicin resistance, and colonies were scored to confirm the absence of the tetracycline resistance marker present on the helper plasmid.

Transposition Experiments Using the ts Donor Plasmid.

Calcium chloride competent cells were prepared from a culture of DH10B containing bacmid (bMON14272.H3) and helper (pMON7124) grown in 2XYT medium containing 50 μg/ml kanamycin and 15 μg/ml tetracycline as described above. One hundred μl competent cells were mixed with 40 ng of the ts donor plasmid pMON18127, heat shocked at 42° C. for 45 seconds, and outgrown in 1 ml S.O.C. medium at 30° C. for 3.5 hours. One hundred μl of cells were plated from undiluted or $10^{-2}$ diluted outgrowth culture on pre-warmed LB agar medium containing 50 μg/ml kanamycin, 10 μg/ml gentamicin, 15 μg/ml tetracycline, 40 μg/ml IPTG and 200 μg/ml bluo-gal and incubated overnight at 44° C. Between 77 and 88% of transformants were white (Lac−) kanamycin-resistant, gentamicin-resistant, and tetracycline-resistant and exhibited a single colony morphology.

Transformants, both Lac− and Lac+, were purified by restreaking on selective media containing kanamycin, gentamicin and tetracycline. Bacmid DNA was isolated from 3-5 ml overnight cultures using either a Magic mini prep kit or Qiawell-8 plasmid prep system. Insertion of the mini-Tn7 into the attTn7 site was verified by PCR using 2 different pairs of primers specific for both the mini-Tn7 element and sequences flanking the attTn7 site in the bacmid. PCR fragments of the expected sizes were observed only from composite bacmid (Lac−) isolates. Bacmid DNA isolated from non-recombinant (Lac+) transformants gave the expected PCR product only when primer pairs were specific for the bacmid DNA alone.

Experiments which directly compare transposition efficiencies obtained from donor molecules which are temperature sensitive or are incompatible with the helper plasmid were performed as described with the following modifications; CaCl$_2$ competent cells transformed with the incompatible donor pMON14327 were outgrown in 1 ml S.O.C. medium at 30° C. or 37° C. for 1-17 hours. The purpose of incubating at the two temperatures was to determine if temperature alone influenced the frequency of transposition. Twenty μl of cells were plated, in triplicate at different time points, directly from the outgrowth culture on LB agar medium containing 50 μg/ml kanamycin, 10 μg/ml gentamicin, 15 μg/ml tetracycline, 40 μg/ml IPTG and 200 μg/ml bluo-gal. Plates were incubated at 37° C. when the outgrowth was performed at 37° C. Plate incubation was at 44° C. when the cultures were outgrown at 30° C.

Over 80% of transformants were white (Lac−) kanamycin-resistant, gentamicin-resistant, and tetracycline-resistant and exhibited a single colony morphology when the donor molecule was the ts plasmid pMON18127. Only 20-25% of transformants were white (Lac−) kanamycin-resistant, gentamicin-resistant, and tetracycline-resistant and exhibited two distinct colony morphologies when the donor molecule was the incompatible pMON14327. Incubation of transformants containing pMON14327 at 44° C. did not increase the frequency of transposition but did delay the time at which the maximal level of Lac− transformants were observed. These results demonstrates that the ts donor molecule provides a more efficient means of generating recombinant baculoviruses.

Transposition experiments using the E. coli chromosome as a donor molecule. When the donor was the chromosome of E. coli DH10B::Tn14327, fifty ng of pMON7124 (helper) was transformed into 100 μl CaCl$_2$ competent DH10B::Tn14327 containing the bacmid bMON14272. Following heat shock at 42° C. for 45 seconds, cells were outgrown in 1 ml S.O.C. medium am 37° C. for 3.5 hours. One hundred ml of cells were plated from undiluted or $10^{-2}$ diluted outgrowth culture on LB agar medium containing 50 μg/ml kanamycin, 10 μg/ml gentamicin, 15 μg/ml tetracycline, 40 μg/ml IPTG and 200 μg/ml bluo-gal and incubated overnight at 37° C.

Typically less than 3% of transformants were white (Lac−) kanamycin-resistant, gentamicin-resistant, and tetracycline-resistant colonies. These results demonstrate that this method is not efficient and is the least effective mode for generating recombinant viruses.

The structure of bacmid DNAs.

DNAs from donor plasmids, the parent bacmids, and the composite bacmids isolated from E. coli and from insect cells were examined by digestion with BglII, EcoRI, I-SceI, NotI, PstI, Sse8387I, and XhoI and compared to the pattern generated by cleavage of wild-type AcNPV DNA purified from budded virus. Bacmid DNAs isolated from E. coli and digested with BglII, PstI, or XhoI have the same or a similar restriction pattern as the corresponding vital DNA isolated originally from insect cells, indicating no gross structural differences between DNAs isolated from the two sources. The plasmid DNA was strikingly clean from contaminating E. coli chromosomal DNA compared to the crude viral DNA prepared from insect cells which was contaminated with insect chromosomal DNA. As expected, the mini-F-Kan-lacZα-mini-attTn7 cassette was inserted into the polyhedrin locus located in the AcNPV restriction fragments BglII-C, PstI-D, and XhoI-D (data not shown). The composite DNAs had a single new insertion of the expected size and location in the mini-attTn7 as judged by the introduction of one or more restriction sites (EcoRI, I-SceI, NotI, Sse8387I) present in the mini-Tn7 donor cassette (data not shown).

EXAMPLE VI

Introduction of a Composite Bacmid into Insect Cells and Expression of the Heterologous Gene When composite bacmid DNAs were isolated from E. coli and transfected into insect cells, cytopathic effects became apparent after 3 days in culture. The cells became swollen and were easily detached from the monolayer compared to mock-infected cells. Cells transfected with a donor plasmid alone did not appear infected.

To rapidly, but qualitatively, assess the ability of the composite viruses to express a heterologous gene, a small amount of media from the transfected cells was mixed with X-gluc, a chromogenic substrate for β-glucuronidase. A dark blue product was observed only in samples taken from cells infected with the composite bacmids vcMON14271::Tn14327, vcMON14272::Tn14327, and vchMON14271::Tn14327/pMON7124, and with the control virus vMON14221 that was constructed by homologous recombination in insect cells. The virus stock vchMON14271::Tn14327/pMON7124 was prepared by transfecting insect cells with a mixture of composite DNA and noninfectious pMON7124 helper plasmid DNA. No β-glucuronidase activity was detectable from uninfected cells or cells infected with wild-type AcNPV, or viruses expressing hLTA$_4$H or hNMT (data not shown). These results indicated that the β-glucuronidase gene under the control of the polyhedrin promoter was expressed when the mini-Tn7 element from the donor plasmid was inserted into the mini-attTn7 site located in the bacmid.

When equivalent amounts of pure composite bacmid DNA (bcMON14271::Tn14327) and a mixture of helper plasmid and composite bacmid DNA that contained the β-glucuronidase gene (bchMON14271::TN14327/pMON7124) were transfected into insect cells, expression of β-glucuronidase qualitatively assessed by reaction of the infected cell supernatents with X-gluc differed at 3 days post-transfection, but not at 5 days post-transfection (data not shown). These results suggest that the difference in expression at the early time point may be due to lower molar ratio of infectious composite bacmid DNA in the mixture compared to amount of the pure composite bacmid DNA that was transfected. Restriction digests indicated that the composite DNA in the mixture accounted for <10% of the DNA, the remainder being the pMON7124 helper plasmid, which would not replicate or be infectious in insect cells (data not shown).

Figure 5:
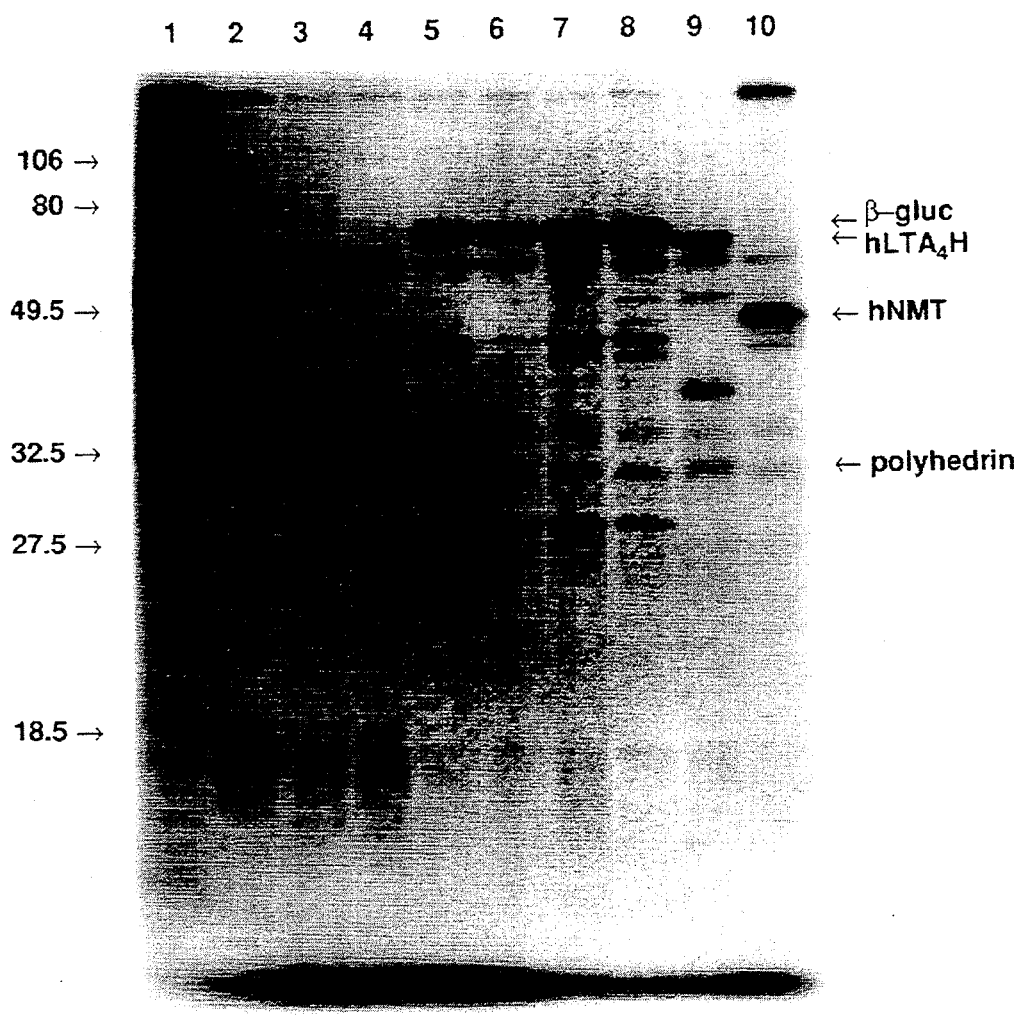

Passage 2 stocks of viruses expressing β-glucuronidase, hLTA4 hydrolase, and hNMT were prepared and titered. The passage 2 stocks of virus were used to infect $6 \times 10^5$ SF21 cells/well in a 24 well plate at a multiplicity of infection of 10 virus particles per cell. The cells were radiolabeled for 4 hours at 44.5 hours post infection with $^{35}$S-methionine. The cells were lysed and samples were separated by SDS-PAGE. An autoradiogram of the resulting gel is shown in FIG. 5. High levels of β-glucuronidase were produced by the control virus vMON14221 (lane 8), and by the composite viruses vcMON14271::Tn14327 (lane 5), vcMON14272::Tn14327 (lane 7), and vchMON14271::Tn14327/pMON7124 (lane 6). The levels of β-glucuronidase expressed by vcMON14271::Tn14327 (lane 5) and vchMON14271::Tn14327/pMON7124 (lane 6) were equivalent, suggesting that the helper DNA present in the mixture of DNAs originally transfected into insect cells simply acts as carrier DNA and is gradually lost from infected cells and that it has no effect on the final expression level observed by the time passage 2 viral stocks are prepared. Slightly higher levels of β-glucuronidase were observed for vcMON14272::Tn14327 (lane 7) compared to vcMON14271::Tn14327 (lane 5) that might be attributed to the orientation of the mini-F-Kan-lacZα-mini-attTn7 cassette within the parent bacmids bMON14271.G2 and bMON14272.H3. Whether this effect will be seen for other heterologous genes inserted into these two bacmids is currently under investigation. The expression of β-glucuronidase by the composite viruses is slightly less than that observed for vMON14221 (lane 8), a recombinant virus constructed in a traditional manner by homologous recombination in insect cells. At least three smaller species were also noted and are probably related to β-glucuronidase, since they are not present in wild-type AcNPV-infected (lane 2) or uninfected cells (lane 1) nor were they detected in cells infected with the parent viruses vMON14271 or vMON14272 (lanes 3 and 4). High levels of human leukotriene A4 hydrolase and human N-myristoyltransferase were expressed by the composite viruses vcMON14271::Tn14314 (lane 9) and vcMON14271::Tn22300 (lane 10). The abundant expression of these heterologous genes demonstrates the general utility of the baculovirus shuttle vector technology to simply and rapidly generate recombinant baculoviruses.

Composite bacmids generated from the experiment comparing the temperature-sensitive and incompatibility methods were isolated and transfected into insect cells. The resultant recombinant viruses were used to evaluate expression of β-glucuronidase at 44 hours post-infection using $^{35}$S methionine labelling. Samples were normalized by BCA protein assay and separated on a 12% SDS-PAGE gel. There was no apparent difference in the levels of protein expression from cells infected with composite bacmids made using ts donor, incompatibility donor or recombinant virus made by traditional methods. These results demonstrate that the temperature-sensitive donor molecule provides a more efficient means for generating recombinant baculoviruses and is considered to be the best mode for foreign gene expression, expression cloning of cDNA and protein engineering in this system.

It is recognized that a number of variations can be made to this invention as it is currently described but which do not depart from the scope and spirit of the invention without compromising any of its advantages. These include substitution of different genetic elements (e.g., drug resistance markers, transposable elements, promoters, heterologous genes, and/or replicons, etc.) on the donor plasmid, the helper plasmid, or the shuttle vector, particularly for improving the efficiency of transposition in *E. coli* or for optimizing the expression of the heterologous gene in the host cell. The helper functions or the donor casstte might also be moved to the attTn7 on the chromosome to improve the efficiency of transposition, by reducing the number of open attTn7 sites in a cell which compete as target sites for transposition in a cell harboring a shuttle vector containing an attTn7 site.

This invention is also directed to any substitution of analogous components. This includes, but is not restricted to, construction of bacterial-eukaryotic cells shuttle vectors using different eukaryotic viruses, use of bacteria other than *E. coli* as a host, use of replicons other than those specified to direct replication of the shuttle vector, the helper functions or the transposable element donor, use of selectable or differentiable genetic markers other than those specified, use of site-specific recombination elements other than those specified, and use of genetic elements for expression in eukaryotic cells other than those specified. It is intended that the scope of the present invention be determined by reference to the appended claims.

REFERENCES CITED

Alting-Mees, M. A., and J. M. Short. 1989. pBluescript II: gene mapping vectors. *Nucl. Acids Res.* 17:9494.

Ausubel, F. M., R. Brent, R. E. Kingston, D. D. Moore, J. G. Seidman, J. A. Smith, K. Struhl, P. Wang-Iverson, and S. G. Bonitz (ed.). 1989. Short Protocols in Molecular Biology: A Compendium of Methods from Current Protocols in Molecular Biology, p. 1–387. Greene Publishing Associates and Wiley-Interscience, New York.

Barry, G. F. 1986. Permanent insertion of foreign genes into the chromosomes of soil bacteria. *Bio/Technology* 4:446–449.

Barry, G. F. 1988. A broad host-range shuttle system for gene insertion into the chromosomes of Gram-negative bacteria. *Gene* 71:75–84.

Berg C. M., D. E. Berg, and E. A. Groisman. 1989. Transposable elements and the genetic engineering of bacteria, p. 879–925. In D. E. Berg, and M. M. Howe (ed.), Mobile DNA. American Society for Microbiology, Washington, D.C.

Brosius, J. 1989. Superpolylinkers in cloning and expression vectors. DNA 8:759–777.

Capone, J. 1989. Screening recombinant baculovirus plaques in situ with antibody probes. Gene Anal. Techn. 6:62–66.

Chung, C. T., S. L. Niemela, and R. H. Miller. 1989. One-step preparation of competent Escherichia coli: Transformation and storage of bacterial cells in the same solution. Proc. Natl. Acad. Sci. USA 86:2172–2175.

Colleaux, L., L. d'Auriol, F. Galibert, and B. Dujon. 1988. Recognition and cleavage site of the intron-encoded omega transposase. Proc. Natl. Acad. Sci. USA 85:6022–6026.

Craig N. L. 1989. Transposon Tn7, p. 211–225. In D. E. Berg, and M. M. Howe (ed.), Mobile DNA. American Society for Microbiology, Washington, D.C.

Dayringer, H. E., and S. A. Sammons. 1991. POLLUX: a program for simulated cloning, mutagenesis and database searching of DNA constructs. CABIOS 7:161–167.

Dente, L., G. Cesareni, and R. Cortese. 1983. pEMBL: A new family of single stranded plasmids. Nucleic Acids Res. 11:1645.

Duronio, R. J., S. I. Reed, and J. I. Gordon. 1992. Mutations of human myristoyl-CoA:protein N-myristoyltransferase cause temperature-sensitive myristic acid auxotrophy in Saccharomyces cerevisiae. Proc. Natl. Acad. Sci. USA 89:4129–33.

Farmer, J. L., R. G. Hampton, and E. Boots. 1989. Flow cytometric assays for monitoring production of recombinant HIV-1 gp160 in insect cells infected with a baculovirus expression vector. J. Virol. Meth. 26:279–290.

Fung, M. C., K. Y. M. Chiu, T. Weber, T. W. Chang and N. T. Chang. 1988. Detection and purification of a recombinant human B lymphotropic virus hhv-6 in the baculovirus expression system by limiting dilution and DNA dot-blot hybridization. J. Virol. Meth. 19:33–42.

Funk, C. D., O. Radmark, J. Y. Fu, T. Matsumoto, H. Jörnvall, T. Shimizu, and Samuelsson. 1987. Molecular cloning and amino acid sequence of leukotriene A4 hydrolase. Proc. Natl. Acad. Sci. USA 84:6677–6681.

Gierse, G. K., V. A. Luckow, S. Aykent, G. S. Bild, B. B. Brightwell, C. P. Rodi, P. M. Sullivan, M. K. Bourner, R. M. Leimgruber, N. M. Kimack, and G. G. Krivi. 1992. High-level expression and purification of human leukotriene A4 hydrolase from insect cells infected with a baculovirus vector. (In preparation)

Grant, S. G. N., J. Jessee, F. R. Bloom, and D. Hanahan. 1990. Differential plasmid rescue from transgenic mouse DNAs into Escherichia coli methylation-restriction mutants. Proc. Natl. Acad. Sci. USA 87:4645–4669.

Hamilton, C. M., M. Aldea, B. Washburn, P. Babitzke, and S. R. Kushner. 1989. New method for generating deletions and gene replacements in Escherichia coli. J. Bacteriol. 171:4617–4622.

Hartig, P. C., and M. C. Cardon. 1992. Rapid efficient production of baculovirus expression vectors. J. Virol. Methods 38:61–70.

Hashimoto, T., and M. Sekiguchi. 1976. Isolation of temperature-sensitive mutants of R plasmid by in vitro mutagenesis with hydroxylamine. J. Bacteriol. 127:1561–1563.

Hashimoto-Gotoh, T., and M. Sekiguchi. 1977. Mutations to temperature sensitivity in R plasmid pSC101. J. Bacteriol. 131:405–412.

Holloway, B., and K. B. Low. 1987. F-prime and R-prime factors, p. 1145–1153. In F. C. Neidhardt (ed.), Escherichia coli and Salmonella typhimurium. American Society for Microbiology, Washington D.C.

Holmes, D. S., and M. Quigley. 1981. A rapid method for the preparation of bacterial plasmids. Anal. Biochem. 14:193–197.

Jefferson, R. A., S. M. Burgess, and D. Hirsh. 1986. $\beta$-glucuronidase from Escherichia coli as a gene fusion marker. Proc. Natl. Acad. Sci. USA 86:8447–8451.

Jessee, J., and K. Blodgett. 1988. MAX Efficiency E. coli DH5$\alpha$F'I Q ™: A new M13 and phagemid host. B. R. L. Focus 10:69.

Kitts, P. A. 1992. A novel virus construct increases the utility of the baculovirus expression system. CLONTECHniques VII:1–3.

Kitts, P. A. 1992. Production of recombinant baculoviruses using linearized viral DNA, p. In C. Richardson (ed.), Baculovirus Expression Protocols, Methods in Molecular Biology, vol. 9. Humana Press, Clifton, N.J. (In press).

Kitts, P. A., M.D. Ayres, and R. D. Possee. 1990. Linearization of baculovirus DNA enhances the recovery of recombinant virus expression vectors. Nucleic Acids Res. 18:5667–5672.

Kline, B. 1985. A review of mini-F plasmid maintenance. Plasmid 14:1–16.

Lichtenstein, C., and S. Brenner. 1982. Unique insertion site of Tn7 in the E. coli chromosome. Nature 297:601–603.

Luckow, V. A. 1991. Cloning and expression of heterologous genes in insect cells with baculovirus vectors., p. 97–152. In A. Prokop, R. K. Bajpai, and C. Ho (ed.), Recombinant DNA Technology and Applications. McGraw-Hill, New York.

Luckow, V. A., and M. D. Summers. 1988. Signals important for high-level expression of foreign genes in Autographa californica nuclear polyhedrosis virus expression vectors. Virology 167:56–71.

Luckow, V. A., and M. D. Summers. 1988. Trends in the development of baculovirus expression vectors. Bio/Technology 6:47–55.

Luckow, V. A., and M. D. Summers. 1989. High level expression of nonfused foreign genes with Autographa californica nuclear polyhedrosis virus expression vector. Virology 70:31–39.

Maeda, S. 1989. Expression of foreign genes in insects using baculovirus vectors. Ann. Rev. Entomol. 34:351–372.

Malitschek, B. and M. Schartl. 1991. Rapid identification of recombinant baculoviruses using PCR. Biotechniques 11:177–178.

Maniatis, T., E. F. Fritsch, and J. Sambrook (ed.). 1982. Molecular Cloning. Cold Spring Harbor, Cold Spring Harbor.

Miller, J. H. 1972. Experiments in Molecular Genetics, p. 1–446. Cold Spring Harbor, Cold Spring Harbor, N.Y.

Miller, L. K. 1988. Baculoviruses as gene expression vectors. Ann. Rev. Microbiol. 42:177–199.

Minami, M., S. Ohno, H. Kawasaki, O. Radmark, B. Samuelsson, H. Jörnvall, T. Shimizu, Y. Seyama, and K. Suzuki. 1987. Molecular cloning of a cDNA coding for human leukotriene A4 hydrolase. Complete primary structure of an enzyme involved in eicosanoid synthesis. *J. Biol. Chem.* 262:13873–13876.

Murhammer, D. W. 1991. The use of insect cell cultures for recombinant protein synthesis: Engineering aspects. *Applied Biochem. Biotechnol.* 31:283–310.

O'Reilly, D. R., L. K. Miller, and V. A. Luckow. 1992. Baculovirus Expression Vectors: A Laboratory Manual, p. 1–347. W. H. Freeman and Company, New York.

Oka, A., H. Sugisaki, and M. Takanami. 1981. Nucleotide sequence of the kanamycin resistance transposon Tn903. *J. Mol. Biol.* 147:217–226.

Patel, G., K. Nasmyth, and N. Jones. 1992. A new method for the isolation of recombinant baculovirus. *Nucl. Acids. Res.* 20:97–104.

Peakman, T. C., R. A. Harris, and D. R. Gewert. 1992. Highly efficient generation of recombinant baculoviruses by enzymatically-mediated site-specific in vitro recombination. Nucl. Acids Res. 20:495–500.

Sambrook, J., E. Fritsch, and T. Maniatis. 1989. Molecular Cloning: A Laboratory Manual, (Second ed.), p. 1–1626. Cold Spring Harbor Laboratory, Cold Spring Harbor, N.Y.

Smith, G. E., and M. D. Summers. 1978. Analysis of baculovirus genomes with restriction endonucleases. *Virology* 89:517–527.

Smith, G. E., and M. D. Summers. 1979. Restriction maps of five *Autographa californica* MNPV variants, *Trichoplusia ni* MNPV and *Galleria mellonella* MNPV DNAs with endonucleases SmaI, KpnI, BamHI, SacI, XhoI, and EcoRI. *J. Virol.* 30:828–838.

Summers, M. D., and G. E. Smith. 1987. A manual of methods for baculovirus vectors and insect cell culture procedures. *Texas Agricultural Experiment Station Bulletin No.* 1555:

Taylor, L., and R. E. Rose. 1988. A correction in the nucleotide sequence of the Tn903 kanamycin resistance determinant in pUC4K. *Nucleic Acids Res.* 16:358.

Vaughn, J. L., R. H. Goodwin, G. J. Tompkins, and P. McCawley. 1977. The establishment of two cell lines from the insect *Spodoptera frugiperda* (Lepidoptera: Noctuidae). *In Vitro* 13:213–217.

Vialard, J., M. Lalumière, T. Vernet, D. Briedis, G. Alkhatib, D. Henning, D. Levin, and C. Richardson. 1990. Synthesis of the membrane fusion and hemagglutinin proteins of measles virus, using a novel baculovirus vector containing the β-galactosidase gene. *J. Virol.* 64:37–50.

Vieira, J., and J. Messing. 1982. The pUC plasmids, an M13mp7-derived system for insertion mutagenesis and sequencing with synthetic universal primers. *Gene* 19:259–268.

Webb, A., M. Bradley, S. Phelan, J. Wu, and L. Gehrke. 1991. Use of the polymerase chain reaction for screening and evaluation of recombinant baculovirus clones. *BioTechniques* 11:512–519.

Wohlleben, W., W. Arnold, L. Bissonnette, A. Pelletier, A. Tanguay, P. H. Roy, G. C. Gamboa, G. F. Barry, E. Aubert, J. Davies, and S. A. Kagan. 1989. On the evolution of Tn21-like multiresistance transposons: Sequence analysis of the gene (aacC1) for gentamicin acetyltransferase-3-I (AAC(3)-I), another member of the Tn21 -based expression cassette. *Mol. Gen. Genet.* 217:202–208.

Zuidema, D., A. Schouten, M. Usmany, A. J. Maule, G. J. Belsham, J. Roosien, E. C. Klinge-Roode, J. W. M. van Lent, and J. M. Vlak. 1990. Expression of cauliflower mosaic virus gene I in insect cells using a novel polyhedrin-based baculovirus expression vector. *J. Gen, Virol.* 71:2201–2209.

---

What is claimed is:

1. A Bacmid, comprising;
   a. a nuclear polyhedrosis virus DNA which includes the elements required for said nuclear polyhedrosis virus DNA propagation in insect cells;
   b. a low copy number bacterial replicon, inserted into a nonessential locus of said nuclear polyhedrosis virus DNA, which drives the replication of said nuclear polyhedrosis virus DNA in bacteria;
   c. a bacterial genetic marker inserted into nonessential locus of said nuclear polyhedrosis virus DNA; and
   d. a preferential target site for the insertion of a transposon inserted into a nonessential locus of said nuclear polyhedrosis virus DNA.

2. A Bacmid as recited in claim 1 wherein said nuclear polyhedrosis virus DNA is a member of the Multiple nucleocapsids per envelope (MNPV) subgenera of the Nuclear polyhedrosis virus (NPV) genera of the Eubaculovirinae subfamliy (occluded baculoviruses) of the Baculoviridae family of insect viruses.

3. A Bacmid as recited in claim 1 wherein said bacterial replicon is mini-F.

4. A Bacmid as recited in claim 1 wherein said bacterial genetic marker is a selectable marker.

5. A Bacmid as recited in claim 1 wherein said preferential target site is attTn7.

6. A Bacmid as recited in claim 1 wherein said bacterium is *E. coli*.

7. The bacmid as recited in claim 1 wherein said bacmid is selected from the group consisting of A.T.C.C. 69059 and 69060.

8. A Bacmid as recited in claim 2 wherein said nuclear polyhedrosis virus DNA is the *Autographa californica* nuclear polyhedrosis virus species of the Multiple nucleocapsids per envelope (MNPV) subgenera of the Nuclear polyhedrosis virus (NPV) genera of the Eubaculovirinae subfamily (occluded baculoviruses) of the Baculoviridae family of insect viruses.

9. A Bacmid as recited in claim 4 wherein said selectable marker confers ampicillin, tetracycline, kanamycin, or gentamicin resistance.

10. A Bacmid as recited in claim 9 wherein said selectable marker confers kanamycin resistance.

11. A donor DNA molecule, comprising:
   a. a bacterial replicon; and
   b. a transposon operably linked to said bacterial replicon that can be transposed site-specifically into a preferential target site and which includes a heterologous DNA and a bacterial genetic marker.

12. The Donor DNA molecule of claim 11 wherein said DNA molecule is a Donor plasmid.

13. The donor DNA molecule of claim 11 wherein said bacterial replicon is the bacterial chromosome.

14. The donor DNA molecule of claim 11 wherein said heterologous DNA is under the control of a promoter which is operable in Eukaryotic host cells.

15. The donor plasmid of claim 12 wherein said transposon is Tn7.

16. The donor plasmid of claim 12 wherein said bacterial replicon is temperature-sensitive.

17. The donor plasmid of claim 12 wherein said bacterial replicon is incompatible with the helper plasmid.

18. The donor plasmid as recited in claim 12 wherein said heterologous DNA is under the control of a promoter which is operable in insect cells.

19. The donor plasmid as recited in claim 12 wherein said donor plasmid is selected from the group consisting of A.T.C.C. 69061 and 69062.

20. A composite Bacmid, comprising:
   a. a nuclear polyhedrosis virus DNA which includes the elements required for said nuclear polyhedrosis virus DNA propagation in insect cells;
   b. a low copy number bacterial replicon, inserted into a nonessential locus of said nuclear polyhedrosis virus DNA, which drives the replication of said nuclear polyhedrosis virus DNA in bacteria;
   c. a first bacterial genetic marker inserted into a nonessential locus of said nuclear polyhedrosis virus DNA;
   d. a preferential target site for the insertion of a transposon inserted into a nonessential locus of said nuclear polyhedrosis virus DNA; and
   e. a transposon, inserted into said preferential target site, which includes heterologous DNA and a second bacterial genetic marker that is different from said first bacterial genetic marker.

21. A composite Bacmid as recited in claim 20 wherein said nuclear polyhedrosis virus DNA is a member of the Multiple nucleocapsids per envelope (MNPV) subgenera of the Nuclear polyhedrosis virus (NPV) genera of the Eubaculovirinae subfamily (occluded baculoviruses) of the Baculoviridae family of insect viruses.

22. A composite bacmid as recited in claim 20 wherein said heterologous DNA is under the control of a promoter that is operable in insect cells.

23. A composite bacmid as recited in claim 20 wherein said bacterial replicon is mini-F.

24. A composite bacmid as recited in claim 20 wherein said bacterial genetic marker is a selectable marker.

25. A composite bacmid as recited in claim 20 wherein said preferential target site is attTn7.

26. A composite bacmid as recited in claim 20 wherein said bacteria are *E. coli*.

27. A composite Bacmid as recited in claim 21 wherein said nuclear polyhedrosis virus DNA is the *Autographa californica* nuclear polyhedrosis virus species of the Multiple nucleocapsids per envelope (MNPV) subgenera of the Nuclear polyhedrosis virus (NPV) genera of the Eubaculovirinae subfamily (occluded baculoviruses) of the Baculoviridae family of insect viruses.

28. A composite bacmid as recited in claim 24 wherein said selectable marker confers ampicillin, tetracycline, kanamycin or gentamicin resistance.

29. A composite bacmid as recited in claim 24 wherein said selectable marker confers kanamycin resistance.

30. A composite bacmid as recited in claim 25 wherein said attTn7 is inserted into the middle of the lacZα region.

31. A method for producing a composite bacmid, which comprises;
   A. introducing into bacteria the following components in any order or all together;
      1. a Bacmid, comprising;
         a. a nuclear polyhedrosis virus DNA which includes the elements required for said nuclear polyhedrosis virus DNA propagation in insect cells;
         b. a low copy number bacterial replicon, inserted into a nonessential locus of said nuclear polyhedrosis virus DNA, which drives the replication of said nuclear polyhedrosis virus DNA in bacteria;
         c. a bacterial genetic marker inserted into a nonessential locus of said nuclear polyhedrosis virus DNA; and
         d. a preferential target site for the insertion of a transposon inserted into a nonessential locus of said nuclear polyhedrosis virus DNA;
      2. a donor DNA molecule, comprising;
         a. a bacterial replicon; and
         b. a transposon operably linked to said bacterial replicon that can be transposed site-specifically into a preferential target site on a bacmid and which includes a heterologous DNA and a bacterial genetic marker.
      3. a helper plasmid,
         wherein components 1, 2 and 3 have different bacterial genetic markers;
   B. Incubating said bacteria;
   C. Identifying bacteria in which transposition has occurred; and
   D. Isolating a composite bacmid from said identified bacteria.

32. The method for producing a composite Bacmid as recited in claim 31 wherein said nuclear polyhedrosis virus DNA is a member of the Multiple nucleocapsids per envelope (MNPV) subgenera of the Nuclear polyhedrosis virus (NPV) genera of the Eubaculovirinae subfamily (occluded baculoviruses) of the Baculoviridae family of insect viruses.

33. The method for producing a composite Bacmid as recited in claim 31 wherein said bacterial replicon is mini-F.

34. The method for producing a composite Bacmid as recited in claim 31 wherein said bacterial genetic marker is a selectable marker.

35. The method for producing a composite Bacmid as recited in claim 31 wherein said preferential target site is attTn7.

36. The method for producing a composite Bacmid as recited in claim 31 wherein said bacteria are *E. coli*.

37. The method for producing a composite Bacmid as recited in claim 31 wherein said nuclear polyhedrosis virus DNA is under the control of a promotor capable of driving the expression of heterologous protein in insect cells.

38. The method for producing a composite Bacmid as recited in claim 32 wherein said nuclear polyhedrosis virus DNA is the *Autographa californica* nuclear polyhedrosis virus species of the Multiple nucleocapsids per envelope (MNPV) subgenera of the Nuclear polyhedrosis virus (NPV) genera of the Eubaculovirinae subfamily (occluded baculoviruses) of the Baculoviridae family of insect viruses.

39. The method for producing a composite Bacmid as recited in claim 34 wherein said selectable marker confers ampicillin, tetracycline, kanamycin, or gentamicin resistance.

40. The method for producing a composite Bacmid as recited in claim 34 wherein said selectable marker confers kanamycin resistance.

41. The method for producing a composite Bacmid as recited in claim 35 wherein said attTn7 is inserted into the middle of the lacZα region.

42. A method of producing heterologous protein in insect cells using a composite bacmid of claim 20 comprising;
   1. Introducing into said insect cells said composite Bacmid;
   2. Incubating said insect cells; and
   3. Isolating said heterologous protein.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
AGATCTGCAG  GAATTCACAT  AACAGGAAGA  AAAATGC                                         37
```

( 2 ) INFORMATION FOR SEQ ID NO:2:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GGATCCGTCG ACAGCCGCGT AACCTGGCAA A   31

( 2 ) INFORMATION FOR SEQ ID NO:3:

( i ) SEQUENCE CHARACTERISTICS:
        ( A ) LENGTH: 52 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TGATCATTAA TTAAGTCTTC GAACCAATAC GCAAACCGCC TCTCCCCGCG CG   52

( 2 ) INFORMATION FOR SEQ ID NO:4:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CGATCGACTC GAGCGTCTTC GAAGCGCGTA ACCACCACAC CCGCCGCGC   49

( 2 ) INFORMATION FOR SEQ ID NO:5:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GAAGACNNNN NN   12

( 2 ) INFORMATION FOR SEQ ID NO:6:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

NNNNNNGTCT TC   12

( 2 ) INFORMATION FOR SEQ ID NO:7:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

TAGGGATAAC AGGGTATT   18

( 2 ) INFORMATION FOR SEQ ID NO:8:

( i ) SEQUENCE CHARACTERISTICS:
        ( A ) LENGTH: 28 base pairs

```
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

GATCCGCTAG GGATAACAGG GTAATATA                                                  2 8

( 2 ) INFORMATION FOR SEQ ID NO:9:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GATCTATATT ACCCTGTTAT CCCTAGCG                                                  2 8
```